(12) United States Patent
Fehr Pereira Lopes

(10) Patent No.: US 10,314,918 B2
(45) Date of Patent: Jun. 11, 2019

(54) JASMONATE DERIVATIVES AND COMPOSITIONS THEREOF

(71) Applicant: Nanocare Technologies, Inc., New York, NY (US)

(72) Inventor: José E. Fehr Pereira Lopes, São Carlos (BR)

(73) Assignee: NANOCARE TECHNOLOGIES, INC., New York, NY (US)

( * ) Notice: Subject to any disclaimer, the term of this patent is extended or adjusted under 35 U.S.C. 154(b) by 0 days.

(21) Appl. No.: 15/540,537

(22) PCT Filed: Dec. 31, 2015

(86) PCT No.: PCT/US2015/068244
§ 371 (c)(1),
(2) Date: Jun. 28, 2017

(87) PCT Pub. No.: WO2016/109779
PCT Pub. Date: Jul. 7, 2016

(65) Prior Publication Data
US 2017/0368186 A1    Dec. 28, 2017

Related U.S. Application Data

(60) Provisional application No. 62/098,704, filed on Dec. 31, 2014.

(51) Int. Cl.
A61K 47/54 (2017.01)

(52) U.S. Cl.
CPC .................. A61K 47/542 (2017.08)

(58) Field of Classification Search
CPC .................................................. A61K 47/542
See application file for complete search history.

(56) References Cited

U.S. PATENT DOCUMENTS

| | | | |
|---|---|---|---|
| 5,662,932 A | 9/1997 | Amselem et al. | |
| 6,469,061 B1 | 10/2002 | Flescher et al. | |
| 6,790,815 B1 | 9/2004 | Bettiol et al. | |
| 7,425,651 B2 | 9/2008 | Flescher et al. | |
| 7,683,211 B2 | 3/2010 | Flescher et al. | |
| 8,883,220 B2 | 11/2014 | Lopes | |
| 9,592,305 B2 | 3/2017 | Lopes | |
| 2002/0173470 A1 | 11/2002 | Flescher et al. | |
| 2003/0224024 A1* | 12/2003 | Leveque ............... | A61K 8/35 424/401 |
| 2004/0209795 A1 | 10/2004 | Vlad | |
| 2008/0044364 A1 | 2/2008 | Carola et al. | |
| 2009/0098200 A1 | 4/2009 | Temtsin Krayz et al. | |
| 2009/0133166 A1 | 5/2009 | Scheer et al. | |
| 2009/0197939 A1 | 8/2009 | Walke et al. | |
| 2009/0291904 A1* | 11/2009 | Kashman ............... | C07C 49/493 514/32 |
| 2010/0160623 A1 | 6/2010 | Strassburger | |
| 2011/0305731 A1 | 12/2011 | Lopes | |
| 2013/0089615 A1* | 4/2013 | Fehr Pereira Lopes ............... | A61K 31/19 424/493 |
| 2013/0203828 A1 | 8/2013 | Chen et al. | |
| 2013/0338120 A1* | 12/2013 | Sang ....................... | C07C 69/78 514/159 |
| 2014/0220132 A1 | 8/2014 | Lopes | |
| 2015/0140110 A1 | 5/2015 | Lopes | |
| 2016/0354312 A1 | 12/2016 | Lopes | |
| 2018/0000958 A1 | 1/2018 | Lopes | |

FOREIGN PATENT DOCUMENTS

| | | |
|---|---|---|
| BR | PI0604024-1 A | 4/2008 |
| CA | 2630666 A1 | 6/2007 |
| CN | 1054605 A | 9/1991 |
| CN | 101818100 A | 9/2010 |
| EP | 0392608 A2 | 10/1990 |
| EP | 1379229 B1 | 2/2007 |
| EP | 1814894 A2 | 8/2007 |
| JP | 10-059829 A | 3/1998 |
| JP | 3568325 B2 | 9/2004 |
| WO | WO 1998/056340 A1 | 12/1998 |
| WO | WO 01/02589 | 1/2001 |
| WO | WO 2002/072011 A2 | 9/2002 |
| WO | WO 2002/080890 A2 | 10/2002 |
| WO | WO 2006/028311 A1 | 3/2006 |
| WO | WO 2006/056308 A2 | 6/2006 |
| WO | WO 2006/068665 A1 | 6/2006 |
| WO | WO 2007/010080 A2 | 1/2007 |
| WO | WO 2007/066336 | 6/2007 |
| WO | WO 2007/066337 | 6/2007 |
| WO | WO 2007/103336 A2 | 9/2007 |
| WO | WO 2007/145663 A1 | 12/2007 |

(Continued)

OTHER PUBLICATIONS

Zaragoza Dorwald (Side Reactions in Organic Synthesis, 2005, WILEY-VCH Verlag GmbH & Co. KGaA, Weinheim, Preface. p. IX . (Year: 2005).*
Zhang et al, Plant Signaling & Behavior, Methyl Jasmonate and its Potential in Cancer Therapy, 2015, 10(9), pp. 1-3, article addendum. (Year: 2015).*
Yeruva et al (Anticancer Drugs, Perillyl alcohol and methyl jasmonate sensitize cancer cells to cisplatin,2010, 21(1), pp. 1-9. (Year: 2010).*

(Continued)

*Primary Examiner* — Paul A Zucker
(74) *Attorney, Agent, or Firm* — Cooley LLP

(57) ABSTRACT

The disclosure describes jasmonate conjugates and nanocarried and/or microcarried jasmonate conjugates and pharmaceutical compositions thereof, as well as use thereof for treating or preventing angiogenesis-related or NF-κB-related disorders. Also disclosed are methods of making the conjugates.

15 Claims, No Drawings

(56) References Cited

FOREIGN PATENT DOCUMENTS

| WO | WO 2008/007367 A1 | 1/2008 |
| WO | WO 2008/083213 A2 | 7/2008 |
| WO | WO 2009/019693 A2 | 2/2009 |
| WO | WO 2009/060165 A2 | 5/2009 |
| WO | WO 2009/106662 A1 | 9/2009 |
| WO | WO 2010/006392 A2 | 1/2010 |
| WO | WO 2010/143180 A1 | 12/2010 |
| WO | WO 2012/114196 A1 | 8/2012 |
| WO | WO 2013/040556 A1 | 3/2013 |
| WO | WO 2013/056754 A1 | 4/2013 |
| WO | WO 2014/009429 | 1/2014 |

OTHER PUBLICATIONS

"Gum Arabic," American Heritage Science Dictionary. 2009 [Online], Nov. 6, 2013. Retrieved from the Internet: <URL: http://www.thefreedictionary.com/Acacia+gum>.

Costantini, P. et al., "Mitochondrion as a Novel Target of Anticancer Chemotherapy," Journal of the National Cancer Institute, vol. 92, No. 13, Jul. 5, 2000, pp. 1042-1053.

Dias, M. L. N. et al., "Pharmacokinetics and tumor uptake of a derivatized form of paclitaxel associated to a cholesterol-rich nanoemulsion (LDE) in patients with gynecologic cancers," Cancer Chemother Pharmacol (2007) 59:105-111.

Drumond, W. S. et al., "Synthesis and Characterization of Poly(lactic acid-b-ethylene glycol) Copolymer," Polimeros: Ciência e Tecnologia, vol. 14, No. 2, (2004), pp. 74-79 (with English Abstract).

Favero, G. M. et al., "Synthetic nanoemulsion resembling a protein-free model of 7-ketocholesterol containing low density lipoprotein: in vitro and in vivo studies," Biol. Res., 43:439-444 (2010).

Fingrut, O. et al., "Jasmonates Induce Nonapoptotic Death in High-Resistance Mutant p53-Expressing B-Lymphoma Cells," Brit. J. Pharmacol., 146 (2005):800-808.

Fingrut, O. et al., "Plant Stress Hormones Suppress the Proliferation and Induce Apoptosis in Human Cancer Cells," Leukemia, 16(4):608-616 (Apr. 2002).

Flescher, E., "Jasmonates—A New Family of Anti-Cancer Agents," Anti-Cancer Drugs, vol. 16, (2005), pp. 911-916.

Flescher, E., "Jasmonates in Cancer Therapy," Cancer Letters 245 (2007) 1-10.

Gfeller, A. et al., "Jasmonate Biochemical Pathway," Science Signaling, vol. 3, No. 109, Feb. 16, 2010, pp. 1-6.

IUPAC Compendium of Chemical Terminology, "Inclusion Compound (inclusion complex)," (2014), 2nd ed. (the "Gold Book"), available online at https://doi.org/10.1351/goldbook.I02998.

Molineux, G., "Pegylation: engineering improved pharmaceuticals for enhanced therapy," Cancer Treatment Reviews 2002; 28(Suppl. A), pp. 13-16.

Palmieri, B. et al., "A preliminary study of the local treatment of preneoplastic and malignant skin lesions using methyl jasmonate," European Review for Medical and Pharmacological Sciences, vol. 15 (2011) 333-336.

Rajewski, R. A. et al., "Pharmaceutical Applications of Cyclodextrins. 2. In Vivo Drug Delivery," J. Pharmaceut. Sci., vol. 85, No. 11 (Nov. 1996), pp. 1142-1169.

Rotem, R. et al., "Jasmonates: Novel Anticancer Agents Acting Directly and Selectively on Human Cancer Cell Mitochondria," Cancer Res., vol. 65, No. 5 (Mar. 1, 2005), pp. 1984-1993.

Swamy, S. G. et al., "Triacontanol and Jasmonic Acid Differentially Modulate the Lipid Organization as Evidenced by the Fluorescent Probe Behavior and $^{31}$P Magnetic Resonance Shifts in Model Membranes," J. Membrane Biol. 228 (2009)165-177.

Maeda, H. et al., "Tumor vascular permeability and the EPR effect in macromolecular therapeutics: a review," Journal of Controlled Release, 2000, vol. 65, pp. 271-284.

Van De Manakker, F. et al., "Cyclodextrin-Based Polymeric Materials: Synthesis, Properties, and Pharmaceutical/Biomedical Applications," Biomacromolecules, 2009, vol. 10, No. 12, pp. 3157-3175.

Maranhao, R. C. et al., "Plasma Kinetics and Biodistribution of a Lipid Emulsion Resembling Low-Density Lipoprotein in Patients with Acute Leukemia," Cancer Research, Sep. 1994, vol. 54, pp. 4660-4666.

Ginsburg, G. S. et al., "Microemulsions of phospholipids and cholesterol esters," The Journal of Biological Chemistry, vol. 257, No. 14, Jul. 25, 1982, pp. 8216-8227.

Wang, Y. et al., "Methyl jasmonate sensitizes human bladder cancer cells to gambogic acid induced apoptosis through down-regulation of EZH2 expression by miR-101," British Journal of Pharmacology, 2014, vol. 171, pp. 618-635.

\* cited by examiner

JASMONATE DERIVATIVES AND COMPOSITIONS THEREOF

RELATED APPLICATION

This application is a U.S. National Phase application, filed under 35 U.S.C. § 371, of International Application No. PCT/US2015/068244, filed Dec. 31. 2015, which claims priority to, and the benefit of, U.S. provisional application No. 62/098,704, filed Dec. 31, 2014, the entire content of each of which are incorporated herein by reference in their entireties.

FIELD OF THE INVENTION

The present invention relates to jasmonate conjugates (e.g., a hybrid compound or a compound prepared or obtained by conjugating, associating, attaching, or connecting a jasmonate compound or any derivative thereof to/with another non-jasmonate compound such as resveratrol, a gambogic acid, perillyl alcohol, curcumin, a flavonoid, or a chemical component of propolis or derivatives thereof) as well as pharmaceutical compositions thereof (e.g., including nanocarried or microcarried jasmonate conjugates) that are useful for the treatment and/or prevention of various diseases and disorders.

BACKGROUND OF THE INVENTION

Jasmonate compounds or jasmonates are characterized by the cyclopentanone ring and are known as plant stress hormones produced by plants facing a stressful situation. Examples of jasmonates include, but are not limited to, jasmonic acid (JA), methyl jasmonate (MJ), and cis-/trans-jasmone (see, e.g., U.S. Pat. No. 6,469,061 and WO 2007/066337). It has been shown that MJ and JA are both effective and selective against tumors cells (see, e.g., Flescher, *Anti-Cancer Drugs* 2005, 16:901-916 and US 2002/0173470). Yet, when administered in vivo, jasmonates are usually metabolized by, e.g., esterases, before they reach target cancer cells, rending them less attractive as anti-cancer agents.

SUMMARY OF THE INVENTION

The terms "jasmonate compounds" and "jasmonates" and the like are used interchangeably herein.

The present invention provides conjugates of a jasmonate compound and one or more other compounds such as, for example, resveratrol, a gambogic acid, perillyl alcohol, curcumin, a flavonoid, 10-hydroxydecenoic acid, acetogenin, phosphatidylethanolamine, or a chemical component of propolis (e.g., phenolic compounds, including phenolic acids, flavonoids, and their derivatives such as caffeic acid, cinnamic acid, and esters thereof, e.g., caffeic acid phenethyl ester (CAPE), and 3,5-diprenyl-4-hydroxycinnamic acid (artepillin C)), or a chemical component of Emu oil, or a chemical component or an extract of bitter gourd (*Momordica charantia*) (e.g., triterpene glycosides or triterpenoid glycosides, such as momordin (saponin), charantin, momordicosides A, B, F1, F2 K—N, and S, charantosides I through VIII, karavilosides I, II, III, V, and XI, MAP30 and MCP30 proteins), kuguaglycoside A through H, goyaglycosides c and d, vitamins, including beta carotene, ascorbic acid, niacin, and thiamin, elemental compounds (eg, iron, iodine, magnesium, sodium, calcium), and fatty acids, including stearic, palmitic, and oleic acids, phenols such as catechin and epicatechin, phenolic acids such as gallic, gentisic, and vanillic acids, as well as lutein, lycopene, carotenes, zeaxanthin, xanthins, and vicine ro vicine-like compounds, and essential oil from bitter melon seeds such as sesquiterepene, phenylpropanoids, and monoterpenes, including nerolidol), Coenzyme $Q_{10}$, a chemical component of Argan oil, a chemical component or an extract of *Euphorbia tirucalli*, or derivatives thereof. For example, the conjugate is formed by reacting a jasmonate compound or a derivative thereof with one or more other compounds to form a covalent bond between the jasmonate compound and the other compound. For example, the covalent bond formed can be biodegradable or non-biodegradable. The one or more other compounds forming the conjugate are different from the jasmonate compound forming the conjugate. For example, the one or more other compounds forming the conjugate are not jasmonate compounds.

The conjugate has the following structure:

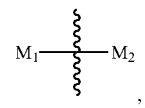

in which $M_1$ is a jasmonate compound or a derivative thereof, $M_2$ is a compound different from $M_1$ and is covalently attached to $M_1$ and

between $M_1$ and $M_2$ denotes direct or indirect attachment of $M_2$ to $M_1$. For example,

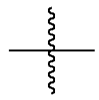

is a single covalent bond formed by reacting one of the functional groups of a jasmonate compound (e.g., hydroxyl (OH) or carbonyl (C=O)) with a functional group of $M_2$ (e.g., carboxylic acid or amine group). For another example,

is a linker moiety formed by, e.g., first derivatizing a jasmonate compound and/or $M_2$ to introduce new functional group(s) and then reacting the derivatized jasmonate compound with $M_2$ or derivatized $M_2$, or vice versa.

The jasmonate compound forming the conjugate, $M_1$, is selected from the group consisting of jasmonic acid, 7-isojasmonic acid, 9,10-dihydrojasmonic acid, 9,10-dihydroisojasmonic acid, 2,3-didehydrojasmonic acid, 3,4-didehydrojasmonic acid, 3,7-didehydrojasmonic acid, 4,5-didehydrojasmonic acid, 4,5-didehydro-7-isojasmonic acid, cucurbic acid, 6-epi-cucurbic acid, 6-epi-cucurbic acid-lactone, 12-hydroxy-jasmonic acid, 12-hydroxy-jasmonic acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside, 5,6-didehydro-jasmonic acid, 6,7-didehydro-jasmonic acid, 7,8-didehydrojasmonic acid, cis-jasmone, dihydrojasmone, and a lower alkyl (i.e., $C_1$-$C_6$ alkyl) ester thereof. For example, the jasmonate compound is methyl jasmonate (MJ), methyl dihydrojasmonate (MDJ, also known as methyl 2-(3-oxo-2-pentylcyclopentyl)acetate) or methyl 4,5-didehydrojasmonate (MDDJ).

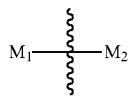

can be synthesized via reactions of a functional group of $M_2$ with any of the carbonyl groups of the jasmonate compound $M_1$, e.g., the ketone (E1) on the cyclopentyl ring of a jasmonate compound (e.g., MJ, MDJ, or MDDJ) or the carbonyl of the ester (E2) of the jasmonate compound. For example, a reaction between the ketone (or ester group) of jasmonate and $M_2$ containing an amine group (MA1) can result in the formation of an imine or a hemiaminal (or amide). As another example, $M_2$ can be first derivatized, e.g., by reducing an aldehyde group of $M_2$ to form a reduced $M_2$ compound ("RM2") or hydrating a double bond in $M_2$ to form RM3. These preliminary steps result in hydroxyl groups in RM2 or RM3, which can react with the ketone (E1) of the jasmonate compound to form a ketal or ester, or react with the ester (E2) group of the jasmonate compound to form a new ester.

The reaction among these compounds, i.e., a jasmonate compound $M_1$, MA1, RM2, and RM3, can generate products including, but not limited to: MA1-(E1)$M_1$; MA1-(E2)$M_1$; MA1-(E1)$M_1$(E2)-MA1; RM2-(E1)$M_1$; RM2-(E2)$M_1$; RM2-(E1)$M_1$(E2)-RM2; RM3-(E1)$M_1$; RM3-(E2)$M_1$; RM3-(E1)$M_1$(E2)-RM3 as well as mixture of them such as MA1-(E1)$M_1$(E2)-RM2; RM2-(E1)$M_1$(E2)-MA1; MA1-(E1)$M_1$(E2)-RM3; RM3-(E1)$M_1$(E2)-MA1; RM2-(E1)$M_1$(E2)-RM3; and RM3-(E1)$M_1$(E2)-RM2.

For example, the conjugate is a hybrid molecule of a jasmonate compound or a derivative thereof and a resveratrol or a derivative thereof ("jasmonate-resveratrol conjugate") via forming an ester bond from the carboxyl group (COOH) of the jasmonate compound and one of the three hydroxyl groups of resveratrol.

For example, the jasmonate-resveratrol conjugate has a chemical structure represented by Formula (I):

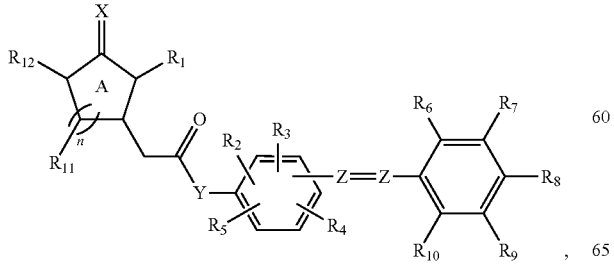

(I)

in which
n is 1, 2, 3, or 4;
X is O or S;
Y is O, NH, or OC(O);
each occurrence of Z independently is CH or N;
$R_1$ is H, alkyl, alkenyl, or alkynyl;
each occurrence of $R_2$, $R_3$, $R_4$, $R_5$, $R_6$, $R_7$, $R_8$, $R_9$, $R_{10}$, $R_{11}$, and $R_{12}$ independently is H, $NH_2$, $NHCOR_{13}$, $-N=CHR_{14}$, $-N=CH-R_{13}$, $-NHCH_2R_{15}$, $-NHCH_2R_{13}$, $-NHSO_2R_{15}$, $-NHCONHR_{15}$, $-N=CHR_{16}$, $-COOR_{16}$, $-CONR_{16}R_{16}$, $-CONR_{16}R_{15}$, $-CN$, $-COCH_2Cl$, $-CONHNH_2$, $R_{17}$, $R_{16}$, $-OR_{16}$, $-SR_{16}$, $-NO_2$, $-COR_{16}$, $-NO$, $-N_3$, $-OCN$, $-NCS$, $-COOR_{16}$, $-COCN$, $-NR_{16}R_{16}$, $-SOR_{16}$, $-SO_2R_{16}$, $-SO_3R_{16}$, $-CH_2OR_{16}$,

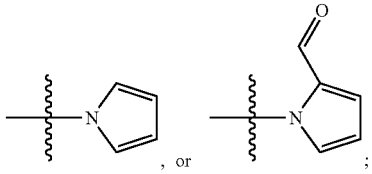 [SMILES: *n1cccc1 ; *n1cccc1C=O]

, or ;

alternatively, when valence permits, any two neighboring $R_{11}$ or neighboring $R_{11}$ and $R_{12}$, together with the two carbon atoms to which they attach, form a carbon-carbon double bond or a cycloalkyl, cycloalkenyl, aryl, heterocycloalkyl, or heteroaryl group;

$R_{13}$ is $R_{14}$, $R_{16}$, $-CH_2OR_{15}$, $-CH=CHR_{15}$, $-CH_2CHR_{15}COR_{16}$, $-C_2H_4OR_{15}$, $-C_3H_6OR_{15}$, $-C_2H_4SCOR_{16}$, $-CH_2SCOR_{16}$, $-COOR_{16}$, $-CH_2S-R_{18}$, $-CH_2-R_{18}$, $-CH=CH-R_{18}$, in which $R_{18}$ is cycloalkyl, 5- or 6-membered heteroaryl, or 5- to 12-memebered heterocycloalkyl and $R_{18}$ is optionally substituted with one or more of $-COOR_{16}$, $R_{16}$ and $R_{17}$;

$R_{14}$ is phenyl optionally substituted with one or more $R_{16}$;
$R_{15}$ is phenyl optionally substituted with one or more substituents selected from $R_{13}$ and $R_{16}$;
$R_{16}$ is H, alkyl optionally substituted with halo or hydroxyl, alkenyl, phenyl, or $-CH_2R_{14}$; and
$R_{17}$ is halo.

In various embodiments, n is 1, i.e., the ring A is a 5-member ring with or without carbon-carbon double bond(s); n is 2, i.e., the ring A is a 6-member ring with or without carbon-carbon double bond(s); n is 3, i.e., the ring A is a 7-member ring with or without carbon-carbon double bond(s); and/or n is 4, i.e., the ring A is a 8-member ring with or without carbon-carbon double bond(s).

For example, the jasmonate-resveratrol conjugate has a chemical structure represented by Formula (Ia) or (Ib) as shown below.

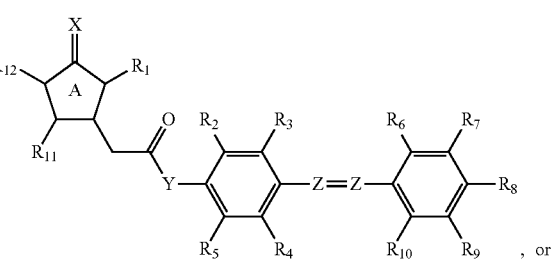

(Ia)

, or

-continued (Ib)

in which X, Y, Z, $R_1$ through $R_{12}$ are as defined herein for Formula (I) above.

For example, the conjugate of Formulae described herein have one or more of the following features when applicable:

The ring A may be fused with any other cycles (e.g. formed by $R_{11}$ and $R_{12}$), which can be heterocyclic, aliphatic or aromatic, to form a substituted or unsubstituted bicyclic, tricyclic, tetracyclic or pentacyclic group which is either saturated or unsaturated.

X is O.
X is S.
Y is O.
Y is NH.
Y is OC(O).
Each Z is CH.
One Z is CH and the other Z is N.
Each Z is N.
Z=Z is the cis-isomerism.
Z=Z is the trans-isomerism.
$R_1$ is selected from one of the following:

—CH$_3$, —C$_2$H$_5$, —C$_3$H$_7$, —C$_4$H$_9$, —C$_5$H$_{11}$, and $R_{13}$ is $R_{14}$, $R_{16}$, —CH$_2$OR$_{15}$, —CH=CHR$_{15}$, —CH$_2$CHR$_{15}$COR$_{16}$, —C$_2$H$_4$OR$_{15}$, —C$_3$H$_6$OR$_{15}$, —C$_2$H$_4$SCOR$_{16}$, —CH$_2$SCOR$_{16}$, —COOR$_{16}$, o-nitrobenzyl, m-nitrobenzyl, p-nitrobenzyl, or a group selected from the following:

-continued $R_{14}$ is $R_{15}$ is $R_{16}$ is —H, —CH$_3$, —C(R$_{17}$)$_3$, —C$_2$H$_5$, —C$_3$H$_7$, —CH(CH$_3$)$_2$, —CH$_2$CH=CH$_2$, —CH=C(CH$_3$)$_2$, —CH=CHCH$_3$, —CH=CHC$_2$H$_5$, —C$_4$H$_9$, —C(CH$_3$)$_3$, -Ph, —CH$_2$R$_{14}$, or C$_2$H$_4$OH.

$R_{17}$ is —F, —Cl, —Br, or —I.

In another embodiment, the conjugate is a hybrid molecule of a jasmonate compound or a derivative thereof and a gambogic acid or a derivative thereof ("jasmonate-gambogic acid conjugate") via, e.g., forming an ester bond from the carboxyl group (COOH) of the jasmonate compound and the hydroxyl group of gambogic acid, or forming a carboxylic anhydride from the carboxyl groups of both the jasmonate compound and gambogic acid.

In yet another embodiment, the conjugate is a hybrid molecule of a jasmonate compound or a derivative thereof and perillyl alcohol or a derivative thereof ("jasmonate-perillyl alcohol conjugate") via, e.g., forming an ester bond from the carboxyl group (COOH) of the jasmonate compound and the hydroxyl group of perillyl alcohol.

In yet another embodiment, the conjugate is a hybrid molecule of a jasmonate compound or a derivative thereof and curcumin or a derivative thereof ("jasmonate-curcumin conjugate") via, e.g., forming an ester bond from the carboxyl group (COOH) of the jasmonate compound and the hydroxyl group of curcumin, or forming a hemiketal (or ketal) from the ketone carbonyl of the jasmonate compound and one (or two) hydroxyl of curcumin or derivatives thereof.

In still another embodiment, the conjugate is a hybrid molecule of a jasmonate compound or a derivative thereof and a chemical component of bitter gourd or a derivative thereof ("jasmonate-bitter gourd component conjugate") via, e.g., forming an ester bond from the carboxyl group (COOH) of the jasmonate compound and one of the hydroxyl groups of a chemical component of bitter gourd.

In still another embodiment, the conjugate is a hybrid molecule of a jasmonate compound or a derivative thereof and Coenzyme Q10 or a derivative thereof ("jasmonate-Coenzyme Q10 conjugate").

Similarly, via the synthetic methods described herein or otherwise known in the art, the conjugate can be a jasmonate-flavonoid conjugate, or a jasmonate-10-hydroxydecenoic acid conjugate, a jasmonate-acetogenin conjugate, a jasmonate-phosphatidylethanolamine conjugate, a jasmonate-caffeic acid/ester conjugate, a jasmonate-cinnamic acid/ester conjugate, a jasmonate-Argan oil conjugate, or a jasmonate-*Euphorbia tirucalli* chemical component conjugate.

In another aspect, the present disclosure provides a pharmaceutical composition including the jasmonate conjugate(s) described herein. For example, the pharmaceutical composition further includes Emu oil or a chemical component of Emu oil. For example, the pharmaceutical composition further includes a pharmaceutically acceptable solvent and a plurality of nanocarriers and/or microcarriers. The nanocarriers and/or the microcarriers are formed of a cyclodextrin or a dendrimer, or a liposome, or are synthetic nanoemulsion particles (LDEs) comprising a cholesteryl ester core surrounded by a phospholipid outer layer; the nanocarriers have a size ranging from 1 nanometer (nm) to 1000 nm (e.g., 1-900 nm, 1-800 nm, 1-700 nm, 1-600 nm, 1-500 nm, 1-400 nm, 1-300 nm, 1-200 nm, 1-100 nm, 1-90 nm, 1-80 nm, 1-70 nm, 1-50 nm, 1-30 nm, or 1-10 nm); the microcarriers have a size ranging from 1 micron to 50 micron (e.g., from 1 micron to about 40, 30, 20, 10, 9, 8, 7, 6, 5, 4, 3, 2, or 1.5 micron) and the pharmaceutical composition has a concentration of conjugate ranging from 1 nM to 1 M (e.g., from 1 nM to 10 nM, 1 nM to 100 nM, 1 nM to 1 µM, 1 nM to 10 µM, 1 nM to 100 µM, 1 nM to 0.005 M, 100 µM to 1 mM, 100 µM to 10 mM, 100 µM to 100 mM, 100 mM to 1 M, or 100 mM to 1 M).

In another aspect, the present disclosure provides a pharmaceutical composition including jasmonate compound $M_1$ and/or the jasmonate conjugate(s) described herein, together with another compound which is different from $M_1$ and the jasmonate conjugate(s). For example, the pharmaceutical composition further includes another compound selected from resveratrol, Coenzyme Q10, a bitter gourd component, a chemical component of Argan oil, a chemical component or an extract of *Euphorbia tirucalli*, a jasmonate conjugate thereof, and a combination thereof. For example, the pharmaceutical composition includes jasmonate compound $M_1$, resveratrol, and a bitter gourd component. For example, the pharmaceutical composition includes jasmonate compound $M_1$, resveratrol, and Coenzyme Q10. For example, the pharmaceutical composition includes a jasmonate conjugate described herein, resveratrol, and a bitter gourd component. For example, the pharmaceutical composition further includes a pharmaceutically acceptable solvent and a plurality of nanocarriers and/or microcarriers. The nanocarriers and/or the microcarriers are formed of a cyclodextrin or a dendrimer, or a liposome, or are synthetic nanoemulsion particles (LDEs) comprising a cholesteryl ester core surrounded by a phospholipid outer layer; the nanocarriers have a size ranging from 1 nanometer (nm) to 1000 nm (e.g., 1-900 nm, 1-800 nm, 1-700 nm, 1-600 nm, 1-500 nm, 1-400 nm, 1-300 nm, 1-200 nm, 1-100 nm, 1-90 nm, 1-80 nm, 1-70 nm, 1-50 nm, 1-30 nm, or 1-10 nm); the microcarriers have a size ranging from 1 micron to 50 micron (e.g., from 1 micron to about 40, 30, 20, 10, 9, 8, 7, 6, 5, 4, 3, 2, or 1.5 micron) and the pharmaceutical composition has a concentration of conjugate ranging from 1 nM to 1 M (e.g., from 1 nM to 10 nM, 1 nM to 100 nM, 1 nM to 1 µM, 1 nM to 10 µM, 1 nM to 100 µM, 1 nM to 0.005 M, 100 µM to 1 mM, 100 µM to 10 mM, 100 µM to 100 mM, 100 mM to 1 M, or 15 mM to 70 mM).

The pharmaceutical composition may have one or more (or all) of the following features.

The pharmaceutical composition has a concentration of the jasmonate conjugate ranging from 1 nM to 10-100 µM (e.g., 1 nM to 10 nM, 10 nM to 100 nM, 100 nM to 1 µM, 1 µM to 10 µM, or 10 µM to 100 µM), or 100 µM to 1 mM (e.g., 100 µM to 200 µM, 300 µM, 400 µM, 500 µM, 600 µM, 700 µM, 800 µM, or to 900 µM), or 100 µM to 10 mM (e.g., from 100 µM, 200 µM, 300 µM, 400 µM, 500 µM, 600 µM, 700 µM, 800 µM, or from 900 µM to 1 mM, 2 mM, 3 mM, 4 mM, 5 mM, 6 mM, 7 mM, 8 mM, 9 mM, or to 10 mM), or 100 µM to 100 mM (e.g., from 100 µM, 200 µM, 300 µM, 400 µM, 500 µM, 600 µM, 700 µM, 800 µM, 900 µM, or from 1 mM to 10 mM, 20 mM, 30 mM, 40 mM, 50 mM, 60 mM, 70 mM, 80 mM, 90 mM, or to 100 mM), or 10 µM to 1 mM (e.g., from 10 µM, 20 µM, 30 µM, 40 µM, 50 µM, 60 µM, 70 µM, 80 µM, or from 90 µM to 0.1 mM, 0.2 mM, 0.3 mM, 0.4 mM, 0.5 mM, 0.6 mM, 0.7 mM, 0.8 mM, 0.9 mM, or to 1 mM), or 1-100 mM (e.g., 1-10 mM, 1-20 mM, 1-30 mM, 1-40 mM, 1-50 mM, 1-60 mM, 1-70 mM, 1-80 mM, 1-90 mM, or 15-70 mM), or 100 mM to 1 M (e.g., from 0.2 M, 0.3 M, 0.4 M, 0.5 M, 0.6 M, 0.7 M, 0.8 M, 0.9 M to 1M).

The nanocarriers are formed of a cyclodextrin and have a size ranging from 3 nm to 100 nm, e.g., 3.5-11 nm, 10-20 nm, 10-30 nm, 10-40 nm, 10-50 nm, 10-60 nm, 10-70 nm, 10-80 nm, 10-90 nm, 20-30 nm, 20-40 nm, 20-50 nm, 20-60 nm, 20-70 nm, 20-80 nm, 20-90 nm, 30-40 nm, 30-50 nm, 30-60 nm, 30-70 nm, 30-80 nm, 30-90 nm, 40-50 nm, 40-60 nm, 40-70 nm, 40-80 nm, 40-90 nm, or 50-60 nm, 50-70 nm, 50-80 nm, 50-90 nm, or 50-100 nm.

The nanocarriers are liposomes or LDEs and have a size ranging from 30 nm to 500 nm, e.g., 50 nm-110 nm, 30 nm to 50 nm, 30 nm to 100 nm, 30 nm to 150 nm, 30 nm to 200 nm, 30 nm to 250 nm 30 nm to 300 nm, 30 nm to 350 nm, 30 nm to 400 nm, or 30 nm to 450 nm.

The microcarriers are liposomes or LDEs and have a size ranging from about 2 µm to 30 µm (e.g., 2-5 µm, 2-10 µm, 2-15 µm, 2-20 µm, or 2-25 µm), about 5 µm to 20 µm (e.g., 5-7.5 µm, 5-10 µm, 5-12.5 µm, 5-15 µm, or 5-17.5 µm), or about 10 µm. Further, the concentration of conjugate ranges from 10-100 µM to 100 mM (e.g., from 50-100 µM or from 100 µM, 200 µM, 300 µM, 400 µM, 500 µM, 600 µM, 700 µM, 800 µM, or from 900 µM to 1 mM, 2 mM, 3 mM, 4 mM, 5 mM, 6 mM, 7 mM, 8 mM, 9 mM, or to 10 mM 10 mM, 20 mM, 30 mM, 40 mM, 50 mM, 60 mM, 70 mM, 80 mM, 90 mM, or to 100 mM) or 100 mM to 1 M (e.g., from 0.2 M, 0.3 M, 0.4 M, 0.5 M, 0.6 M, 0.7 M, 0.8 M, 0.9 M to 1M).

The nanocarriers are formed of a dendrimer and have a size ranging from 1 nm to 500 nm (e.g., 2-10 nm, 2-20 nm, 2-50 nm, 2-100 nm, 2-150 nm, 2-200 nm, 2-250 nm, 2-300 nm, 2-350 nm, 2-400 nm, 2-450 nm, 10-100 nm, 10-200 nm, 10-300 nm, 10-400 nm, 10-500 nm, 50-100 nm, 50-200 nm, 50-300 nm, 50-400 nm, 50-500 nm, 100-300 nm, 100-500 nm, 200-500 nm 300-500 nm, or 400-500 nm).

The dendrimer is polyamidoamine (PAMAM).

The concentration of the conjugate ranges from 1 nM to 10-100 µM (e.g., 1 nM to 10 nM, 10 nM to 100 nM, 100 nM to 1 µM, 1 µM to 10 µM, or 10 µM to 100 µM), 10-100 µM to 100 mM (e.g., from 50-100 µM or from 100 µM, 200 µM, 300 µM, 400 µM, 500 µM, 600 µM, 700 µM, 800 µM, or from 900 µM to 1 mM, 2 mM, 3 mM, 4 mM, 5 mM, 6 mM, 7 mM, 8 mM, 9 mM, or to 10 mM 10 mM, 20 mM, 30 mM, 40 mM, 50 mM, 60 mM, 70 mM, 80 mM, 90 mM, or to 100 mM), or 100 mM to 1M (e.g., from 0.2 M, 0.3 M, 0.4 M, 0.5 M, 0.6 M, 0.7 M, 0.8 M, 0.9 M to 1M). For example, the concentration of the conjugate is from 100 µM to 1 mM or 50 nM to 70 nM.

The nanocarriers or microcarriers further contain 2-aminoethyl dihydrogen phosphate (or phosphoethanolamine), 3,7-dimethyl-2,6-octadienal (or citral), methyl salicylate, abscisic acid, natural amino acids, $Ca^{2+}$, $Zn^{2+}$, or derivatives or analogues thereof 3,7-Dimethyl-2,6-octadienal can either be a cis- or trans-isomer.

The pharmaceutically acceptable solvent is water, an alcohol, or a mixture thereof.

In yet another aspect, the present disclosure describes the use of the jasmonate conjugates or their pharmaceutical compositions described herein for the treatment or prevention of an angiogenesis-related disorder, such as cancer or an inflammatory disorder (e.g., inflammatory bowel disorder, acute dermatitis, pelvic inflammatory disorder, or tonsillitis).

In still another aspect, the present disclosure describes use of the jasmonate conjugates or their pharmaceutical compositions described herein for the treatment or prevention of an NF-κB-related disorder, such as a viral, bacterial, or fungal infection.

Further, the invention features use of the jasmonate conjugates or their pharmaceutical compositions described herein for inhibiting cancer cell growth in vitro or in vivo. For example, cancer cell lines suitable for use in the methods of this invention include: UACC62-melanoma, MCF7-cancer resistance, NCIADR-multiple drug resistant breast cancer, 7860-kidney cancer, NC1460-lung cancer, PCO3-prostate cancer resistance, OVCAR03-ovary Cancer, HT29-Colon Cancer, K562-leukemia, TCP-1003 (Triple-Negative Breast Cancer Panel 3), Caco-2-colon cancer, a panel of 18 triple-negative breast tumor cell lines sharing a mesenchymal-like or luminal morphology; breast cancer cell lines HCC38 (ATCC® Number: CRL-2314™) and MCF7 (ATCC® Number: HTB-22™); prostate adenocarcinoma cell line PC-3 (ATCC® Number: CRL-1435™); prostate cancer cell line VCaP (ATCC® Number: CRL-2876™); prostate carcinoma cell line 22Rv1 (ATCC® Number: CRL-2505™); prostate carcinoma cell line DU 145 (ATCC® Number: HTB-81™); prostate carcinoma cell line LNCaP clone FGC (ATCC® Number: CRL-1740™); leukemia cell line MOLT-4 (ATCC® Number: CLR-1582™); leukemia (AML) cell line KG-1 (ATCC® Number: CCL-246™); leukemia (CML) cell line K-562 (ATCC® Number: CCL-243™); leukemia human cell line CCRF-CEM (ATCC® Number: CCL-119™); CLL leukemia cell line Hs 505.T (ATCC® Number: CRL-7306™); Jurkat cell line (leukemia, ATCC® Number: TIB-156™); Molm cell lines (leukemia, e.g., Molm-13, Molm-14, Molm-16, Molm-17, and Molm-18), Nomo cell lines (leukemia, e.g., NOMO-1) and Ras mutant cells.

The present disclosure also describes methods of synthesizing the jasmonate conjugates or their pharmaceutical compositions, and methods of using them for treating various disorders.

DETAILED DESCRIPTION

Jasmonates have been found to be potential anticancer agents acting directly and selectively on human cancer cell mitochondria (see, e.g., Rotem et al., *Cancer Res* 2005; 65:1984-1993; Costantini et al., JNCI 2000; 90:1042-1053) It has been reported that members of jasmonates, and some of their synthetic derivatives, exhibit anti-cancer activity in vitro and in vivo. For example, jasmonates increased the life span of EL-4 lymphoma-bearing mice, MJ is active in chemo-resistant B-lymphoma cells, and preliminary data has suggested that MJ exhibits cytotoxicity via apoptotic pathway (see, e.g., Flescher, *Cancer Lett.* 2007; 245(1-2):1-10; Fingrut et al., *Br J Pharmacol.* 2005; 146(6): 800-808; Fingrut et al., *Leukemia*, 2002; 16:608-616.) Mechanisms of action have been proposed to explain the anti-cancer activity of jasmonates (See id). However, the major problem facing this new family of anti-cancer agents is the difficulty to administer the compounds in vivo. Being an ester, when administered in vivo, jasmonates are usually metabolized by, e.g., esterases, before they reach target cancer cells, rending them less attractive as anti-cancer agents.

The invention provides jasmonate conjugates that are suitable for pharmaceutical use and pharmaceutical compositions thereof. The invention is based in part upon the unexpected discovery that jasmonate conjugates are more selective and/or potent than the parent molecules. The invention is also based in part upon the unexpected discovery that jasmonate conjugates have improved bioavailability. For example, the jasmonate conjugates described herein can be delivered with or without a nano-/micro-carrier such as cyclodextrin.

As used in the specification and the appended claims, the singular forms "a," "an," and "the" include plural referents unless the context clearly dictates otherwise. Thus, for example, reference to "a jasmonate compound" may include not only a single jasmonate but also a combination or mixture of two or more different jasmonates including prodrugs, esters, salts, derivatives, and/or metabolites thereof.

As used herein, the phrases "for example," "for instance," "such as," or "including" are meant to introduce examples that further clarify more general subject matter. These examples are provided only as an aid for understanding the disclosure, and are not meant to be limiting in any fashion.

In describing and claiming the present invention, the following terminology will be used in accordance with the definitions set out below.

As used herein, the phrase "containing," "being formed/composed of," "including," "having the formula," or "having the structure" is not intended to be limiting and is used in the same way that the term "comprising" is commonly used unless the context clearly dictates otherwise.

The term "nanocarrier" as used herein refers to a carrier or vehicle suitable for carrying and delivering an active ingredient (e.g., a drug) to a target cell, tissue, or organ and the vehicle has a size in the range of about 1 nanometer (nm) to about 1000 nm. The term "microcarrier" as used herein refers to a carrier or vehicle suitable for carrying and delivering an active ingredient (e.g., a drug) to a target cell, tissue, or organ and the vehicle has a size in the range of about 1 micron to about 100 micron. In one embodiment, a microcarrier is formed of a cluster of nanocarriers, e.g., an LDE microcarrier formed of a cluster of LDE nanocarriers. Preferably, the nanocarrier or microcarrier is a pharmaceutically acceptable carrier.

The term "nanocarried/microcarried compound/conjugate" or the term "nanocarrier/microcarrier containing a compound/conjugate" as used herein refers to a complex of a nanocarrier/microcarrier associated or coupled with a compound or conjugate. The association or coupling can be created via a chemical bond (e.g., a covalent bond), a hydrogen bond, a van der Waals force, a Coulomb interaction, or the like. In one embodiment, the compound is encapsulated in the nanocarrier/microcarrier. In another embodiment, the compound is partially encapsulated in the nanocarrier/microcarrier or at the surface of the nanocarrier/microcarrier (e.g., either as a part of the nanocarrier/microcarrier surface or outside yet attached to the surface).

The term "emulsion" refers to a suspension of small globules or particles of a first liquid (the dispersed phase) dispersed in a second liquid (the continuous phase), with which the first is normally immiscible.

The terms "nanoemulsion" and "microemulsion" are used interchangeably herein and, as used herein, refer to an emulsion having the dispersed particles with a size ranging from about 1 nm to about 50 μm (e.g., 1 nm-50 μm, 1 nm-40 μm, 1 nm-30 μm, 1 nm-20 μm, 1 nm-10 μm, 1-5000 nm, 1-4000 nm, 1-3000 nm, 1-2000 nm, 1-1000 nm, 1-900 nm, 1-800 nm, 1-700 nm, 1-600 nm, 1-500 nm, 1-400 nm, 1-300 nm, 1-200 nm, 1-150 nm, 1-100 nm, 1-90 nm, 1-80 nm, 1-70 nm, 1-60 nm, 1-50 nm, 1-40 nm, 1-30 nm, 1-20 nm, 1-10 nm, 1-5 nm, 50-100 nm, 3-150 nm, or 3-20 nm). Nanoemulsions tend to appear clear due to the small size of the dispersed phase.

The term "LDE" refers to a nanoemulsion particle that resembles low-density lipoprotein (LDL) in composition and behavior. For example, once introduced into the circulation system, various plasma proteins (e.g., apoE) become absorbed onto the surface of LDE particles and subsequently direct the LDE to cells expressing LDL receptors (LDLR). LDE is protein free and is typically composed of a cholesteryl ester core surrounded by a phospholipid monolayer. For more detailed descriptions of LDEs and their preparations, see, e.g., Ginsburg et al. (1982), *J Biol Chem* 257: 8216-8227; Maranhao et al. (1993), *Lipids* 28: 691-696; and Favero et al. (2010), *Biol Res* 43: 439-444. The term "LDE' is used herein to refer to one example of a liposome-like nanocarrier or microcarrier that can be used in accordance with the instant invention. Determination of other suitable liposome-like nanocarriers and/or microcarriers is within the routine level of skill in the art.

The term "cholesteryl ester" refers to an ester of cholesterol. For example, the ester bond is formed between the carboxylate group of a fatty acid and the hydroxyl group of cholesterol. Examples of cholesteryl esters include but are not limited to cholesteryl oleate, cholesteryl nervonate, etc.

The term "phospholipid" refers to a class of lipids which are a major component of all cell membranes as they can form lipid bilayers. Most phospholipids contain a diglyceride, a phosphate group, and a simple organic molecule such as choline. One exception to this rule is sphingomyelin, which is derived from sphingosine instead of glycerol.

Examples of phospholipids include but are not limited to glycerophospholipid such as phosphatidic acid, phosphatidylethanolamine, phosphatidylcholine, phosphatidylserine, and phosphoinositides (e.g., phosphatidylinositol, phosphatidylinositol phosphate, phosphatidylinositol bisphosphate and phosphatidylinositol triphosphate).

The present invention is intended to include all isomers of the hybrid compounds or conjugates described herein, which refer to and include, optical isomers, and tautomeric isomers, where optical isomers include enantiomers and diastereomers, chiral isomers and non-chiral isomers, and the optical isomers include isolated optical isomers as well as mixtures of optical isomers including racemic and non-racemic mixtures; where an isomer may be in isolated form or in a mixture with one or more other isomers.

Any of the compounds mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated. For example, the jasmonate compound or conjugates thereof described herein includes all of any optical isomer that is based on the asymmetric carbon and is optically pure, any mixture of various optical isomers, or racemic form. Examples of stereoisomers of MDJ include, for example, (1R,2R)-dihydromethyljasmonate, (1R,2S)-dihydromethyljasmonate, (1S,2R)-dihydromethyljasmonate, and (1S,2S)-dihydromethyljasmonate. Examples of isomers of methyl jasmonate include cis- or trans-(1R,2R)-methyl jasmonate, cis- or trans-(1R,2S)-methyl jasmonate, cis- or trans-(1S,2R)-methyl jasmonate, and cis- or trans-(1S,2S)-methyl jasmonate.

The present invention is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

The term "alkyl" as used herein refers to a branched or unbranched saturated hydrocarbon group typically although not necessarily containing 1 to about 24 carbon atoms, such as methyl, ethyl, n-propyl, isopropyl, n-butyl, isobutyl, t-butyl, octyl, decyl, and the like, as well as cycloalkyl groups such as cyclopentyl, cyclohexyl and the like. Generally, although not necessarily, alkyl groups herein may contain 1 to about 18 carbon atoms, and such groups may contain 1 to about 12 carbon atoms. The term "lower alkyl" intends an alkyl group of 1 to 6 carbon atoms, for example, 1, 2, 3, 4, 5, or 6 carbon atoms.

"Alkenyl" includes unsaturated aliphatic groups analogous in length and possible substitution to the alkyls described above, but that contain at least one double bond. For example, the term "alkenyl" includes straight chain alkenyl groups (e.g., ethenyl, propenyl, butenyl, pentenyl, hexenyl, heptenyl, octenyl, nonenyl, decenyl), and branched alkenyl groups. In certain embodiments, a straight chain or branched alkenyl group has six or fewer carbon atoms in its backbone (e.g., $C_2$-$C_6$ for straight chain, $C_3$-$C_6$ for branched chain). The term "$C_2$-$C_6$" includes alkenyl groups containing two to six carbon atoms. The term "$C_3$-$C_6$" includes alkenyl groups containing three to six carbon atoms.

The term "optionally substituted alkenyl" refers to unsubstituted alkenyl or alkenyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, heterocyclyl, alkylaryl, or an aromatic or heteroaromatic moiety.

"Alkynyl" includes unsaturated aliphatic groups analogous in length and possible substitution to the alkyls described above, but which contain at least one triple bond. For example, "alkynyl" includes straight chain alkynyl groups (e.g., ethynyl, propynyl, butynyl, pentynyl, hexynyl, heptynyl, octynyl, nonynyl, decynyl), and branched alkynyl groups. In certain embodiments, a straight chain or branched alkynyl group has six or fewer carbon atoms in its backbone (e.g., $C_2$-$C_6$ for straight chain, $C_3$-$C_6$ for branched chain). The term "$C_2$-$C_6$" includes alkynyl groups containing two to six carbon atoms. The term "$C_3$-$C_6$" includes alkynyl groups containing three to six carbon atoms.

The term "optionally substituted alkynyl" refers to unsubstituted alkynyl or alkynyl having designated substituents replacing one or more hydrogen atoms on one or more hydrocarbon backbone carbon atoms. Such substituents can include, for example, alkyl, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Other optionally substituted moieties (such as optionally substituted cycloalkyl, heterocycloalkyl, aryl, or heteroaryl) include both the unsubstituted moieties and the moieties having one or more of the designated substituents. For example, substituted heterocycloalkyl includes those substituted with one or more alkyl groups, such as 2,2,6,6-tetramethyl-piperidinyl and 2,2,6,6-tetramethyl-1,2,3,6-tetrahydropyridinyl.

"Aryl" includes groups with aromaticity, including "conjugated," or multicyclic systems with at least one aromatic ring and do not contain any heteroatom in the ring structure. Examples include phenyl, benzyl, 1,2,3,4-tetrahydronaphthalenyl, etc.

"Heteroaryl" groups are aryl groups, as defined above, except having from one to four heteroatoms in the ring structure, and may also be referred to as "aryl heterocycles" or "heteroaromatics." As used herein, the term "heteroaryl" is intended to include a stable 5-, 6-, or 7-membered monocyclic or 7-, 8-, 9-, 10-, 11- or 12-membered bicyclic aromatic heterocyclic ring which consists of carbon atoms and one or more heteroatoms, e.g., 1 or 1-2 or 1-3 or 1-4 or 1-5 or 1-6 heteroatoms, or e.g. 1, 2, 3, 4, 5, or 6 heteroatoms, independently selected from the group consisting of nitrogen, oxygen and sulfur. The nitrogen atom may be substituted or unsubstituted (i.e., N or NR wherein R is H or other substituents, as defined). The nitrogen and sulfur heteroatoms may optionally be oxidized (i.e., N→O and $S(O)_p$, where p=1 or 2). It is to be noted that total number of S and O atoms in the aromatic heterocycle is not more than 1.

Examples of heteroaryl groups include pyrrole, furan, thiophene, thiazole, isothiazole, imidazole, triazole, tetrazole, pyrazole, oxazole, isoxazole, pyridine, pyrazine, pyridazine, pyrimidine, and the like.

Furthermore, the terms "aryl" and "heteroaryl" include multicyclic aryl and heteroaryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, naphthrydine, indole, benzofuran, purine, benzofuran, deazapurine, indolizine.

In the case of multicyclic aromatic rings, only one of the rings needs to be aromatic (e.g., 2,3-dihydroindole), although all of the rings may be aromatic (e.g., quinoline). The second ring can also be fused or bridged.

The cycloalkyl, heterocycloalkyl, aryl, or heteroaryl ring can be substituted at one or more ring positions (e.g., the ring-forming carbon or heteroatom such as N) with such substituents as described above, for example, alkyl, alkenyl, alkynyl, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, amino (including alkylamino, dialkylamino, arylamino, diarylamino and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl and heteroaryl groups can also be fused or bridged with alicyclic or heterocyclic rings, which are not aromatic so as to form a multicyclic system (e.g., tetralin, methylenedioxyphenyl).

As used herein, the term "cycloalkyl" refers to a saturated or unsaturated nonaromatic hydrocarbon mono- or multi-ring (e.g., fused, bridged, or spiro rings) system having 3 to 30 carbon atoms (e.g., $C_3$-$C_{10}$). Examples of cycloalkyl include, but are not limited to, cyclopropyl, cyclobutyl, cyclopentyl, cyclohexyl, cycloheptyl, cyclooctyl, cyclopentenyl, cyclohexenyl, cycloheptenyl, and adamantyl. The term "heterocycloalkyl" refers to a saturated or unsaturated nonaromatic 3-8 membered monocyclic, 7-12 membered bicyclic (fused, bridged, or spiro rings), or 11-14 membered tricyclic ring system (fused, bridged, or spiro rings) having one or more heteroatoms (such as O, N, S, or Se), unless specified otherwise. Examples of heterocycloalkyl groups include, but are not limited to, piperidinyl, piperazinyl, pyrrolidinyl, dioxanyl, tetrahydrofuranyl, isoindolinyl, indolinyl, imidazolidinyl, pyrazolidinyl, oxazolidinyl, isoxazolidinyl, triazolidinyl, tetrahyrofuranyl, oxiranyl, azetidinyl, oxetanyl, thietanyl, 1,2,3,6-tetrahydropyridinyl, tetrahydropyranyl, dihydropyranyl, pyranyl, morpholinyl, 1,4-diazepanyl, 1,4-oxazepanyl, 2-oxa-5-azabicyclo[2.2.1]heptanyl, 2,5-diazabicyclo[2.2.1]heptanyl, 2-oxa-6-azaspiro[3.3]heptanyl, 2,6-diazaspiro[3.3]heptanyl, 1,4-dioxa-8-azaspiro[4.5]decanyl and the like.

The term "derivative" as used herein refers to a compound that is derived from a parent compound by some chemical or physical process. It is also used to mean that a compound can arise from another compound, if one atom is replaced with another atom or group of atoms. A term "structural analogue" can be also used for this meaning.

The term "structural analogue" or "analogue" is used to describe structural and functional similarity. Extended to drugs, this definition implies that the analogue of an existing drug molecule shares structural and pharmacological similarities with the original compound. Formally, this definition allows the establishment of three categories of drug analogues: analogues possessing chemical and pharmacological similarities (direct analogues); analogues possessing structural similarities only (structural analogues); and chemically different compounds displaying similar pharmacological properties (functional analogues).

As used herein, "biodegradable" conjugates, compounds or moieties are those that, when taken up by cells, can be broken down by the lysosomal or other chemical machinery or by hydrolysis into components that the cells can either reuse or dispose of without significant toxic effect on the cells. The term "biocleavable" as used herein has the same meaning of "biodegradable". The degradation fragments preferably induce little or no organ or cell overload or pathological processes caused by such overload or other adverse effects in vivo. Examples of biodegradation processes include enzymatic and non-enzymatic hydrolysis, oxidation and reduction. Suitable conditions for non-enzymatic hydrolysis of the biodegradable conjugates (or their components, e.g., the biodegradable linkers between the jasmonate compound and the other molecule) described herein, for example, include exposure of the biodegradable conjugates to water at a temperature and a pH of lysosomal intracellular compartment. Biodegradation of some conjugates (or their components, e.g., the biodegradable linkers between the jasmonate compound and the other molecule), can also be enhanced extracellularly, e.g., in low pH regions of the animal body, e.g., an inflamed area, in the close vicinity of activated macrophages or other cells releasing degradation facilitating factors.

Jasmonate Conjugates

The present invention provides jasmonate conjugates formed by conjugating a jasmonate compound or derivatives thereof and one or more other compounds. The terms "conjugate," "hybrid compound," and "hybrid molecule" are used interchangeably herein.

Examples of said one or more other compounds include but are not limited to, for example, resveratrol, a gambogic acid, perillyl alcohol, curcumin, a flavonoid, 10-hydroxydecenoic acid, acetogenin, phosphatidylethanolamine, or a chemical component of propolis (e.g., phenolic compounds, including phenols, polyphenols, phenolic acids, flavonoids, and their derivatives such as caffeic acid, cinnamic acid, and esters thereof, e.g., caffeic acid phenethyl ester (CAPE), and 3,5-diprenyl-4-hydroxycinnamic acid (artepillin C)), or a chemical component of Emu oil, or a chemical component of bitter gourd (*Momordica charantia*) (e.g., triterpene glycosides or triterpenoid glycosides, such as momordin (saponin), charantin, momordicosides A, B, F1, F2 K—N, and S, charantosides I through VIII, karavilosides I, II, III, V, and XI, MAP30 and MCP30 proteins), kuguaglycoside A through H, goyaglycosides c and d, vitamins, including beta carotene, ascorbic acid, niacin, and thiamin, elemental compounds (eg, iron, iodine, magnesium, sodium, calcium), and fatty acids, including stearic, palmitic, and oleic acids, phenols such as catechin and epicatechin, phenolic acids such as gallic, gentisic, and vanillic acids, as well as lutein, lycopene, carotenes, zeaxanthin, xanthins, and vicine ro vicine-like compounds, and essential oil from bitter melon seeds such as sesquiterepene, phenylpropanoids, and monoterpenes, including nerolidol), Coenzyme $Q_{10}$, a chemical component of Argan oil, a chemical component or an extract of *Euphorbia tirucalli*, or derivatives thereof.

For example, the conjugate is formed by reacting a jasmonate compound or a derivative thereof with one or more other compounds to form a covalent bond between the jasmonate compound and the other compound. For example, the covalent bond formed is biodegradable. For example, the covalent bond formed is not biodegradable. For example, the one or more other compounds forming the conjugate are different from the jasmonate compound forming the conjugate. For example, the one or more other compounds forming the conjugate are not jasmonate compounds.

For example, the conjugate has the following structure:

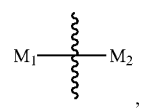

in which $M_1$ is a jasmonate compound or a derivative thereof, $M_2$ is a compound different from $M_1$ and is covalently attached to $M_1$ and

between $M_1$ and $M_2$ denotes direct or indirect attachment of $M_2$ to $M_1$. For example,

is a single covalent bond formed by reacting one of the functional groups of a jasmonate compound (e.g., hydroxyl (OH) or carbonyl (C═O)) with a functional group of $M_2$ (e.g., carboxylic acid or amine group). For another example,

is a linker moiety formed by, e.g., first derivatizing a jasmonate compound and/or $M_2$ to introduce new functional group(s) and then reacting the derivatized jasmonate compound with $M_2$ or derivatized $M_2$, or vice versa.

For example, the jasmonate compound, $M_1$, is selected from the group consisting of jasmonic acid, 7-iso-jasmonic acid, 9,10-dihydrojasmonic acid, 9,10-dihydro-isojasmonic acid, 2,3-didehydrojasmonic acid, 3,4-didehydrojasmonic acid, 3,7-didehydrojasmonic acid, 4,5-didehydrojasmonic acid, 4,5-didehydro-7-isojasmonic acid, cucurbic acid, 6-epi-cucurbic acid, 6-epi-cucurbic acid-lactone, 12-hydroxy-jasmonic acid, 12-hydroxy-jasmonic acid-lactone, 11-hydroxy-jasmonic acid, 8-hydroxy-jasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside, 5,6-didehydro-jasmonic acid, 6,7-didehydro-jasmonic acid, 7,8-didehydro-jasmonic acid, cis-jasmone, dihydrojasmone, and a lower alkyl (i.e., $C_1$-$C_6$ alkyl) ester thereof. For example, the jasmonate compound is methyl jasmonate (MJ), methyl dihydrojasmonate (MDJ, also known as methyl 2-(3-oxo-2-pentylcyclopentyl)acetate) or methyl 4,5-didehydrojasmonate (MDDJ). Other examples of the jasmonate compound suitable for the invention can be found in, e.g., e.g., U.S. Pat. Nos. 6,469,061, 7,425,651 and 7,683,211, WO 02/080890, WO2011/120114, and Gfeller et al. *Sci. Signal.* 2010, Vol. 3, Issue 109, pp. cm3.

For example,

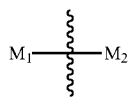

can be synthesized via reactions of a functional group of $M_2$ with any of the carbonyl groups of the jasmonate compound $M_1$, e.g., the ketone (E1) on the cyclopentyl ring of a jasmonate compound (e.g., MJ, MDJ, or MDDJ) or the carbonyl of the ester (E2) of the jasmonate compound. For example, a reaction between the ketone (or ester group) of jasmonate and $M_2$ containing an amine group (MA1) of can result in the formation of an imine or a hemiaminal (or amide). As another example, $M_2$ can be first derivatized, e.g., by reducing an aldehyde group of $M_2$ to form a reduced $M_2$ compound ("RM2") or hydrating a double bond in $M_2$ to form RM3. These preliminary steps result in hydroxyl groups in RM2 or RM3, which can react with the ketone (E1) of the jasmonate compound to form a ketal or ester, or react with the ester (E2) group of the jasmonate compound to form a new ester.

The reaction among these compounds, i.e., a jasmonate compound $M_1$, MA1, RM2, and RM3, can generate products including, but not limited to: MA1-(E1)$M_1$; MA1-(E2)$M_1$; MA1-(E1)$M_1$(E2)-MA1; RM2-(E1)$M_1$; RM2-(E2)$M_1$; RM2-(E1)$M_1$(E2)-RM2; RM3-(E1)$M_1$; RM3-(E2)$M_1$; RM3-(E1)$M_1$(E2)-RM3 as well as mixture of them such as MA1-(E1)$M_1$(E2)-RM2; RM2-(E1)$M_1$(E2)-MA1; MA1-(E1)$M_1$(E2)-RM3; RM3-(E1)$M_1$(E2)-MA1; RM2-(E1)$M_1$(E2)-RM3; RM3-(E1)$M_1$(E2)-RM2.

For example, the conjugate is a hybrid molecule of a jasmonate compound or a derivative thereof and a resveratrol or a derivative thereof ("jasmonate-resveratrol conjugate") via forming an ester bond from the carboxyl group (COOH) of the jasmonate compound and one of the three hydroxyl groups of resveratrol.

For example, the jasmonate-resveratrol conjugate has a chemical structure represented by Formula (I):

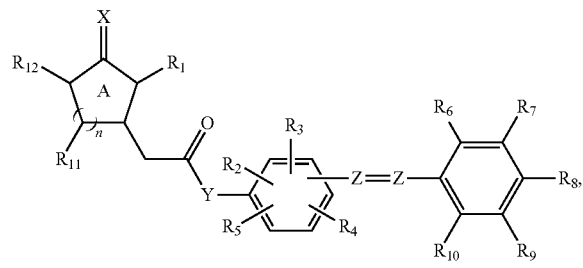

(I)

in which
n is 1, 2, 3, or 4;
X is O or S;
Y is O, NH, or OC(O);
each occurrence of Z independently is CH or N;
$R_1$ is H, alkyl, alkenyl, or alkynyl;
each occurrence of $R_2$, $R_3$, $R_4$, $R_5$, $R_6$, $R_7$, $R_8$, $R_9$, $R_{10}$, $R_{11}$, and $R_{12}$ independently is H, $NH_2$, $NHCOR_{13}$, $-N=CHR_{14}$, $-N=CH-R_{13}$, $-NHCH_2R_{15}$, $-NHCH_2R_{13}$, $-NHSO_2R_{15}$, $-NHCONHR_{15}$, $-N=CHR_{16}$, $-COOR_{16}$, $-CONR_{16}R_{16}$, $-CONR_{16}R_{15}$, $-CN$, $-COCH_2Cl$, $-CONHNH_2$, $R_{17}$, $R_{16}$, $-OR_{16}$, $-SR_{16}$, $-NO_2$, $-COR_{16}$, $-NO$, $-N_3$, $-OCN$, $-NCS$, $-COOR_{16}$, $-COCN$, $-NR_{16}R_{16}$, $-SOR_{16}$, $-SO_2R_{16}$, $-SO_3R_{16}$, $-CH_2OR_{16}$,

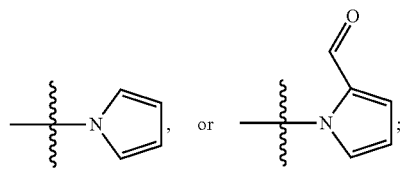 [SMILES: *n1cccc1 ; *n1cccc1C=O]

alternatively, when valence permits, any two neighboring $R_{11}$ or neighboring $R_{11}$ and $R_{12}$, together with the two carbon atoms to which they attach, form a carbon-carbon double bond or a cycloalkyl, cycloalkenyl, aryl, heterocycloalkyl, or heteroaryl group;

$R_{13}$ is $R_{14}$, $R_{16}$, $-CH_2OR_{15}$, $-CH=CHR_{15}$, $-CH_2CHR_{15}COR_{16}$, $-C_2H_4OR_{15}$, $-C_3H_6OR_{15}$, $-C_2H_4SCOR_{16}$, $-CH_2SCOR_{16}$, $-COOR_{16}$, $-CH_2S-R_{18}$, $-CH_2-R_{18}$, $-CH=CH-R_{18}$, in which $R_{18}$ is cycloalkyl, 5- or 6-membered heteroaryl, or 5- to 12-membered heterocycloalkyl and $R_{18}$ is optionally substituted with one or more of $-COOR_{16}$, $R_{16}$ and $R_{17}$;

$R_{14}$ is phenyl optionally substituted with one or more $R_{16}$;
$R_{15}$ is phenyl optionally substituted with one or more substituents selected from $R_{13}$ and $R_{16}$;
$R_{16}$ is H, alkyl optionally substituted with halo or hydroxyl, alkenyl, phenyl, or $-CH_2R_{14}$; and
$R_{17}$ is halo.

For example, n is 1, i.e., the ring A is a 5-member ring with or without carbon-carbon double bond(s).
For example, n is 2, i.e., the ring A is a 6-member ring with or without carbon-carbon double bond(s).
For example, n is 3, i.e., the ring A is a 7-member ring with or without carbon-carbon double bond(s).
For example, n is 4, i.e., the ring A is a 8-member ring with or without carbon-carbon double bond(s).

For example, the jasmonate-resveratrol conjugate has a chemical structure represented by Formula (Ia) or (Ib) as shown below.

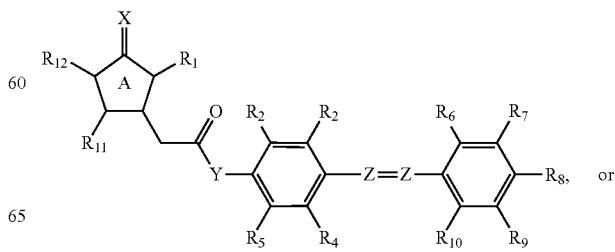

(Ia)

in which X, Y, Z, $R_1$ through $R_{12}$ are as defined herein for Formula (I) above.

For example, the conjugate of Formulae described herein have one or more of the following features when applicable.

For example, the ring A may be fused with any other cycles (e.g. formed by $R_{11}$ and $R_{12}$), which can be heterocyclic, aliphatic or aromatic, to form a substituted or unsubstituted bicyclic, tricyclic, tetracyclic or pentacyclic group which is either saturated or unsaturated.

For example, X is O.
For example, X is S.
For example, Y is O.
For example, Y is NH.
For example, Y is OC(O).
For example, each Z is CH.
For example, one Z is CH and the other Z is N.
For example, each Z is N.
For example, Z=Z is the cis-isomerism.
For example, Z=Z is the trans-isomerism.
For example, $R_1$ is selected from one of the following:

—$CH_3$, —$C_2H_5$, —$C_3H_7$, —$C_4H_9$, —$C_5H_{11}$,

[alkyne group], [allyl group],

[cis-alkene group], and [alkene group].

For example, $R_{13}$ is $R_{14}$, $R_{16}$, —$CH_2OR_{15}$, —CH=$CHR_{15}$, —$CH_2CHR_{15}COR_{16}$, —$C_2H_4OR_{15}$, —$C_3H_6OR_{15}$, —$C_2H_4SCOR_{16}$, —$CH_2SCOR_{16}$, —$COOR_{16}$, o-nitrobenzyl, m-nitrobenzyl, p-nitrobenzyl, or a group selected from the following:

[various heterocyclic and cyclic groups shown including furan, thiophene, pyridine, pyrazine, piperazine, morpholine, piperidine, pyrazole, cyclopropyl, cyclobutyl, cyclopentyl, cyclohexyl derivatives]

For example, $R_{14}$ is

[phenyl with $R_{16}$ substituent]

For example, $R_{15}$ is

[phenyl with $R_{16}$ and $R_{13}$ substituents]

For example, $R_{16}$ is —H, —$CH_3$, —$C(R_{17})_3$, —$C_2H_5$, —$C_3H_7$, —$CH(CH_3)_2$, —$CH_2CH$=$CH_2$, —CH=$C(CH_3)_2$, —CH=$CHCH_3$, —CH=$CHC_2H_5$, —$C_4H_9$, —$C(CH_3)_3$, -Ph, —$CH_2R_{14}$, or $C_2H_4OH$.

For example, $R_{17}$ is —F, —Cl, —Br, or —I.

In another embodiment, the conjugate is a hybrid molecule of a jasmonate compound or a derivative thereof and a gambogic acid or a derivative thereof ("jasmonate-gambogic acid conjugate") via, e.g., forming an ester bond from the carboxyl group (COOH) of the jasmonate compound and the hydroxyl group of gambogic acid, or forming a carboxylic anhydride from the carboxyl groups of both the jasmonate compound and gambogic acid.

In yet another embodiment, the conjugate is a hybrid molecule of a jasmonate compound or a derivative thereof and perillyl alcohol or a derivative thereof ("jasmonate-perillyl alcohol conjugate") via, e.g., forming an ester bond from the carboxyl group (COOH) of the jasmonate compound and the hydroxyl group of perillyl alcohol. For example, the conjugate is of Formula (II):

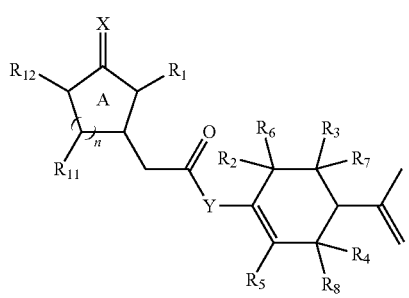

(II)

in which n, X, Y, $R_1$ through $R_8$, $R_{11}$, $R_{12}$ are as defined herein for Formula (I) above.

ketal) from the ketone carbonyl of the jasmonate compound and one (or two) hydroxyl of curcumin or derivatives thereof. For example, the conjugate is of Formula (III):

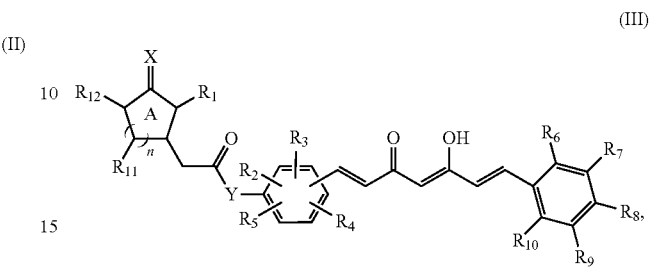

(III)

in which n, X, Y, $R_1$ through $R_{12}$ are as defined herein for Formula (I) above. For another example, the conjugate is of Formula (IVa) or (IVb):

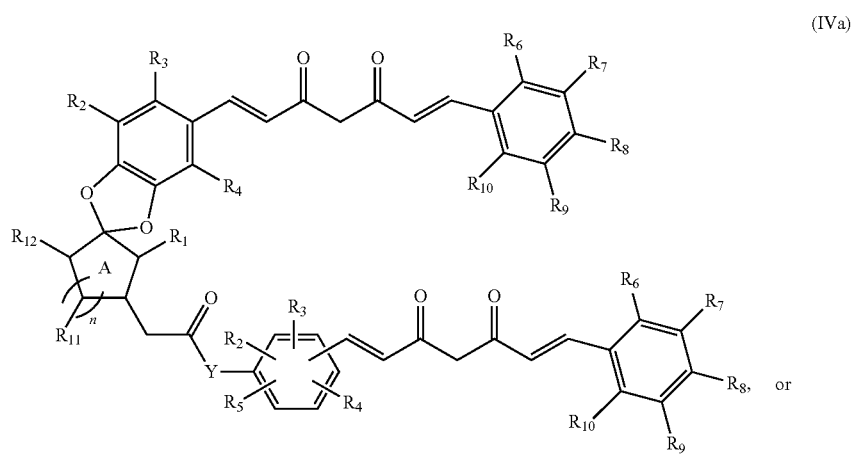

(IVa)

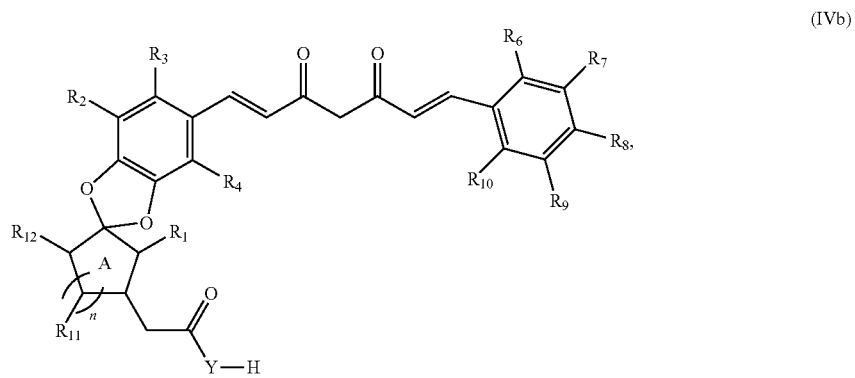

(IVb)

In yet another embodiment, the conjugate is a hybrid molecule of a jasmonate compound or a derivative thereof and curcumin or a derivative thereof ("jasmonate-curcumin conjugate") via, e.g., forming an ester bond from the carboxyl group (COOH) of the jasmonate compound and the hydroxyl group of curcumin, or forming a hemiketal (or in which n, X, Y, $R_1$ through $R_{12}$ are as defined herein for Formula (I) above.

Similarly, via the synthetic methods described herein, the conjugate can be a jasmonate-flavonoid conjugate, or a jasmonate-10-hydroxydecenoic acid conjugate, a jasmonate-acetogenin conjugate, a jasmonate-phosphatidylethanolamine conjugate, a jasmonate-caffeic acid/ester conjugate, or a jasmonate-cinnamic acid/ester conjugate. For another example, the conjugate is of Formula (Va), (Vb), or (Vc):

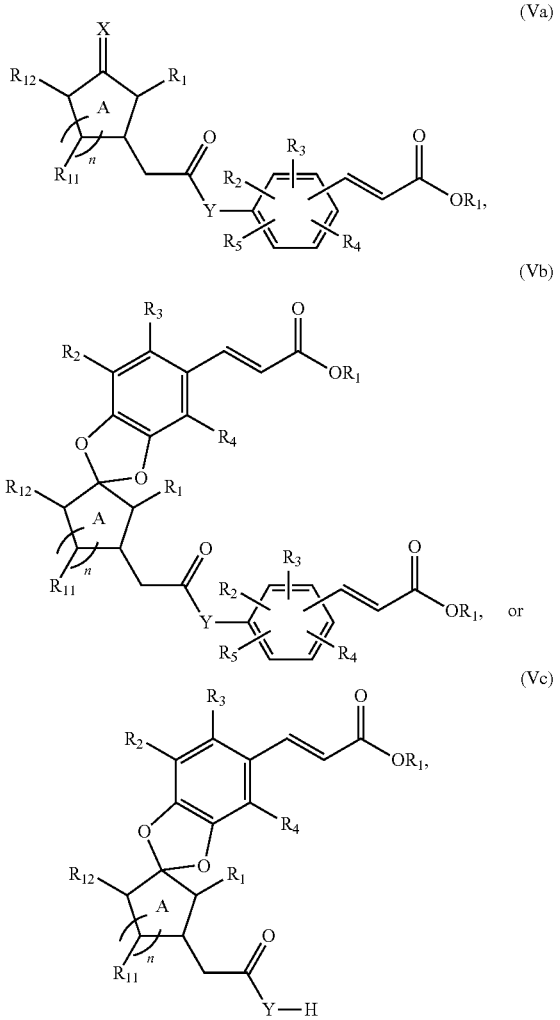

in which n, X, Y, $R_1$ through $R_4$, $R_{11}$ and $R_{12}$ are as defined herein for Formula (I) above. For another example, the conjugate is of Formula (Vd):

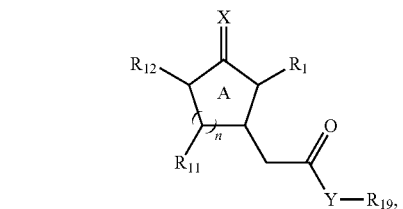

in which n, X, Y, $R_{11}$ and $R_{12}$ are as defined herein for Formula (I) above and $R_{19}$ is $C_4$-$C_{30}$ alkyl or $C_4$-$C_{30}$ alkenyl, each optionally substituted with one or more $OR_1$ or $COOR_1$, in which $R_1$ is H, alkyl, alkenyl, or alkynyl. For example, $R_{19}$ is the aliphatic chain portion of a fatty acid such as oleic acid, alpha-oleic acid, and gamma-oleic acid, e.g., $R_{19}$ is $-(CH_2)_7CH=CH(CH_2)_7CH_3$. For example, $R_{19}$ is the aliphatic chain portion of 10-hydroxy-2-decenoic acid, e.g., $R_{19}$ is $-CH=CH-(CH_2)_7-OH$ or $-(CH_2)_7-CH=CH-COOH$.

The conjugation between cyclopentanone or cyclopentenone and the chemical components of Emu oil take place preferentially at the carboxylic acid functional groups of said components, preferentially oleic acid, alpha-oleic acid, and gamma-oleic acid, which are 70% of the chemical components of Emu oil, and the final hybridized molecules may or may not be carried by nano- or microcarriers.

The conjugation between cyclopentanone or cyclopentenone and the chemical components of propolis, preferentially of the green, black and red types, will take place preferentially through the alcohol functional groups of said components, preferentially flavonoids, phenols and polyphenols, and the final hybridized molecules may or may not be carried by nano- or microcarriers.

The same is true for the rest of the molecules described in this patent application, which, formed by the hybridization of elements of the jasmonate family with 10-hydroxy-2-decenoic acid (10-HDA) may prevent the action of the VEGF (Vascular endothelial growth factor), which induces angiogenesis, thus preventing endothelial cell proliferation and migration and inhibiting revascularization of the tumor area. Proteins or glycoproteins, like albumins 1, 2 and 3, also stimulate macrophages to produce the TNF-alpha anti-tumor factor, like the members of the jasmonate family.

The bonds between cyclopentanones and the following substances, of which may be bound in Emu oil, as well as the cyclopentanones and/or cyclopentenones, or both at the same time, which may be bound to each other, in the sites described, such as albumins, meletins, solenopsins, pederins, conotoxins and kinins, with these substances in their natural and/or pure states or mixed with other substances, as well as structurally modified, which may be used, for example, in the treatment of burns and wounds based on the release of cytokinins and alpha-TNF from macrophages and monocytes.

These substances promote an increase in the synergy of the cyclopentanones and of the cyclopentenones; in addition, they may have the same effect when combined with Emu oil. As a known example found in the literature, the effects of the albumin proteins, the main components of royal jelly, may, in addition to the effects mentioned, be used as a cosmetic in facial rejuvenation. Another classic example is the use of melittin, which is established in the global literature. Melittin has an allergenic effect is present in bee venom; it is responsible for pain and inflammation, resulting in hypersensitivity. This effect is caused by the activation of the inflammation process pathways, which is activated by the prostaglandin cascade. This effect is dose-dependent. When melittin is applied at lower doses, it activates the immune system, like the known elements found in insect venoms.

Conotoxins, a group of neurotoxic peptides isolated from the venoms of sea snails belonging to the genus Conus, are another example. They are peptides that consist of 10 to 30 amino acid residues, which typically have disulfide bonds. Conotoxins have a variety of actions, many of which have not yet been fully explained.

However, five conotoxins have had their actions determined; each one with its specific target:

α-conotoxin inhibits acetylcholine receptors in nerves and muscles;

δ-conotoxin inhibits voltage-dependent sodium channels;

κ-conotoxin inhibits potassium channels;

µ-conotoxin inhibits voltage-dependent sodium channels in muscles; and,

ω-conotoxin inhibits N-type voltage dependent calcium channels.

The peptides found in marine snail venom are so powerful that even small doses are enough to alleviate pain without secondary risks. This association with Emu oil and with cyclopentanones and cyclopentenones, alone or in combination, may have a positive synergistic effect in the treatment of burns and the pain they cause.

This disclosure also provides any hybrid molecules of a jasmonate compound or derivative thereof and a chemical component of bitter gourd (*Momordica charantia*) (e.g., triterpene glycosides or triterpenoid glycosides, such as momordin (saponin), charantin, momordicosides A, B, F1, F2 K—N, and S, charantosides I through VIII, karavilosides I, II, III, V, and XI, MAP30 and MCP30 proteins), kuguaglycoside A through H, goyaglycosides c and d, vitamins, including beta carotene, ascorbic acid, niacin, and thiamin, elemental compounds (eg, iron, iodine, magnesium, sodium, calcium), and fatty acids, including stearic, palmitic, and oleic acids, phenols such as catechin and epicatechin, phenolic acids such as gallic, gentisic, and vanillic acids, as well as lutein, lycopene, carotenes, zeaxanthin, xanthins, and vicine ro vicine-like compounds, and essential oil from bitter melon seeds such as sesquiterepene, phenylpropanoids, and monoterpenes, including nerolidol). Other chemical components of bitter gourd (*Momordica charantia*) are known in the art and can be found in, e.g., the World Wide Web: drugs.com/npp/bitter-melon.html and the following references, the contents of each of which are incorporated by reference herein in their entireties:

1. *Momordica charantia* L. USDA, NRCS. 2007. The PLANTS Database (http://plants.usda.gov, April, 2010). National Plant Data Center, Baton Rouge, La. 70874-4490 USA.
2. Chevallier A. Encyclopedia of Medicinal Plants. New York, N.Y.: DK Publishing; 1996:234.
3. Cunnick J, et al. Bitter Melon (*Momordica charantia*). J Nat Med. 1993; 4:16-21.
4. Duke J. CRC Handbook of Medicinal Herbs. Boca Raton, Fla.: CRC Press Inc; 1989:315-316.
5. Khanna P, Jain S C, Panagariya A, Dixit V P. Hypoglycemic activity of polypeptide-p from a plant source. J Nat Prod. 1981; 44(6):648-655.
6. Raman A, et al. Anti-diabetic properties and phytochemistry of *Momordica charantia* L. (Cucurbitaceae). Phytomedicine. 1996; 2:349-362.
7. Ng T B, Wong C M, Li W W, Yeung H W. Insulin-like molecules in *Momordica charantia* seeds. J Ethnopharmacol. 1986; 15(1):107-117.
8. Horax R, Hettiarachchy N, Chen P. Extraction, quantification, and antioxidant activities of phenolics from pericarp and seeds of bitter melons (*Momordica charantia*) harvested at three maturity stages (immature, mature, and ripe). J Agric Food Chem. 2010; 58(7):4428-4433.
9. Braca A, Siciliano T, D'Arrigo M, Germanò M P. Chemical composition and antimicrobial activity of *Momordica charantia* seed essential oil. Fitoterapia. 2008; 79(2):123-125.
10. Leung L, Birtwhistle R, Kotecha J, Hannah S, Cuthbertson S. Anti-diabetic and hypoglycaemic effects of *Momordica charantia* (bitter melon): a mini review. Br J Nutr. 2009; 102(12):1703-1708.
11. Ooi C P, Yassin Z, Hamid T A. *Momordica charantia* for type 2 diabetes mellitus. Cochrane Database Syst Rev. 2010; 2:CD007845.
12. Basch E, Gabardi S, Ulbricht C. Bitter melon (*Momordica charantia*): a review of efficacy and safety. Am J Health Syst Pharm. 2003; 60(4):356-359.
13. Coutinho H D, Costa J G, Falcão-Silva V S, Siqueira-Júnior J P, Lima E O. Effect of *Momordica charantia* L. in the resistance to aminoglycosides in methicilin-resistant *Staphylococcus aureus*. Comp Immunol Microbiol Infect Dis. 2009 Sep. 2. [Epub ahead of print].
14. Dong C J, Yang X D, Liu J Y. Enzymatic properties of a recombinant phospholipid hydroperoxide glutathione peroxidase from *Momordica charantia* and its complementation function in yeast. Biochemistry (Mosc). 2009; 74(5):502-508.
15. Thenmozhi A J, Subramanian P. Antioxidant Potential of *Momordica charantia* in Ammonium Chloride-induced Hyperammonemic Rats. Evid Based Complement Alternat Med. 2010 Jan. 4. [Epub ahead of print].
16. Ray R B, Raychoudhuri A, Steele R, Nerurkar P. Bitter melon (*Momordica charantia*) extract inhibits breast cancer cell proliferation by modulating cell cycle regulatory genes and promotes apoptosis. Cancer Res. 2010; 70(5): 1925-1931.
17. Xiang L, Huang X, Chen L, Rao P, Ke L. The reparative effects of *Momordica Charantia* Linn. extract on HIT-T15 pancreatic beta-cells. Asia Pac J Clin Nutr. 2007; (16) (suppl 1):249-252.
18. Grossmann M E, Mizuno N K, Dammen M L, Schuster T, Ray A, Cleary M P. Eleostearic Acid inhibits breast cancer proliferation by means of an oxidation-dependent mechanism. Cancer Prev Res (Phila). 2009; 2(10):879-886.
19. Li M, Chen Y, Liu Z, Shen F, Bian X, Meng Y. Anti-tumor activity and immunological modification of ribosome-inactivating protein (RIP) from *Momordica charantia* by covalent attachment of polyethylene glycol. Acta Biochim Biophys Sin (Shanghai). 2009; 41(9):792-799.
20. Huang L, Adachi T, Shimizu Y, et al. Characterization of lectin isolated from *Momordica charantia* seed as a B cell activator. Immunol Lett. 2008; 121(2):148-156.
21. Huang L, Ikejiri A, Shimizu Y, et al. Immunoadjuvant activity of crude lectin extracted from *Momordica charantia* seed. J Vet Med Sci. 2008; 70(5):533-535.
22. Ono T, Tsuji T, Sakai M, et al. Induction of hepatocyte growth factor production in human dermal fibroblasts and their proliferation by the extract of bitter melon pulp. Cytokine. 2009; 46(1):119-126.
23. Ernst E. Herbal medicinal products during pregnancy: are they safe? BJOG. 2002; 109(3):227-235.
24. Chang F, et al. Studies on the antifertility chemical constituents of balsam pear. Chin Tradit Herb Drugs. 1995; 26:281-284.
25. Appiah-Opong R, Commandeur J N, Axson C, Vermeulen N P. Interactions between cytochromes P450, glutathione S-transferases and Ghanaian medicinal plants. Food Chem Toxicol. 2008; 46(12):3598-3603.
26. Erden I, Ordu S, Erden E C, Caglar S O. A case of atrial fibrillation due to *Momordica charantia* (bitter melon). Ann Saudi Med. 2010; 30(1):86-87.

Bitter gourd is also known as bitter apple, wild cucumber, bitter cucumber, balsam apple, balsam pear, margose, lakwa, leprosy gourd; karela; kugua; cerasee, and *Momordica charantia* (see, e.g., at the World Wide Web: mskcc.org/cancer-care/integrative-medicine/herbs/bitter-melon, the content of which is incorporated by reference). All of these terms are used interchangeably herein.

This disclosure also provides any hybrid molecules of a jasmonate compound or derivative thereof and Coenzyme $Q_{10}$.

This disclosure also provides any hybrid molecules of a jasmonate compound or derivative thereof and a chemical component of Argan oil. This disclosure further provides any hybrid molecules of a jasmonate compound or derivative thereof and a chemical component or an extract of *Euphorbia tirucalli*.

This disclosure also provides any hybrid molecules of components of animal venoms, a jasmonate compound or derivative thereof, and/or Emu oil that could bind to the abovementioned sites.

The hybrid molecules of the invention are formed by conjugation of two or more active principles, maintaining the structural characteristics of the precursors, and are more selective and potent. The hybrid molecules, which can be called pro-drugs, may act through two different action mechanisms, because of interactions with different receptors or compartments of the human cell or in any biochemical step of these cells' metabolic pathways. More specifically, while the part of the molecule that is similar to the jasmonate family derivatives may interfere with the mitochondrial membrane's selective permeability and lead to permeability defects—the Warburg effect—, the part that is structurally similar to resveratrol prevents the formation of free radicals, which are essential elements for the peroxidase as well as the mutational elements that destroy normal cells. In other words, besides the molecule's selective action in transformed cells giving rise to the capastic process, the remaining cells will be protected and thus will not progress towards the growing mutational degenerative process.

Regarding the remaining active principles related to the jasmonate family derivatives, pro-drugs that are structurally similar to 10-hydroxydecenoic acid or phosphatidylethanolamine or acetogenins or any component of Emu oil may, as described above, exhibit synergy, with the action mechanisms of the jasmonate family derivatives, and/or with the latter molecules. 10-Hydroxydecenoic acid may prevent the action of VEGF, which induces angiogenesis, thus preventing endothelial cell proliferation and migration and inhibiting revascularization of the tumor area.

Acetogenins, including the annonaceous acetogenins, which are present in the fruit of *Annona muricata*, exercise their action in cancerous cells by reducing the ATP levels through inhibition of Complex I (NADH dehydrogenase) of the electron transport chain and through inhibition of the ubiquinones expressed in the cell membranes of tumor cells.

Pharmaceutical or Cosmetic Compositions

The present invention also provides pharmaceutical compositions comprising a jasmonate conjugate and at least one pharmaceutically acceptable excipient or carrier, e.g., a nanocarrier/microcarrier described herein.

The present invention also provides cosmetic compositions comprising a jasmonate conjugate and at least one cosmetically acceptable excipient or carrier, e.g., a nanocarrier/microcarrier described herein.

The present invention also provides pharmaceutical or cosmetic compositions comprising jasmonate compound $M_1$ and/or the jasmonate conjugate(s) described herein, another compound which is different from $M_1$ and the jasmonate conjugate(s) a jasmonate conjugate, and at least one pharmaceutically or cosmetically acceptable excipient or carrier, e.g., a nanocarrier/microcarrier described herein. For example, the pharmaceutical composition includes jasmonate compound $M_1$ and/or the jasmonate conjugate(s) described herein and another compound selected from resveratrol, Coenzyme Q10, a bitter gourd component, a chemical component of Argan oil, a chemical component or an extract of *Euphorbia tirucalli*, a jasmonate conjugate thereof, or a combination thereof. For example, the ratio (either weight or molar) between the jasmonate compound or conjugate thereof and another compound is 1:1.

In one embodiment, the nanocarriers used for the composition of the invention are formed of cyclodextrins. Cyclodextrins (CDs) are cyclic oligosaccharides formed by D-L (+)-Glucose units linked by a-1,4-C—O—C chains. CDs are produced from starch by means of enzymatic conversion. The native CDs are defined by the number of glucose units, for example, α-, β- and γ-CDs consist of 6, 7, and 8 glucose units, respectively. Other examples of CDs include (2-hydroxypropyl)-β-cyclodextrin, (2-hydroxyethyl)-β-cyclodextrin, methyl-β-cyclodextrin, (2-hydroxypropyl)-γ-cyclodextrin, (2-hydroxypropyl)-α-cyclodextrin, carboxymethyl-β-cyclodextrin, (2-carboxyethyl)-β-cyclodextrin, triacetyl-β-cyclodextrin, acetyl-β-cyclodextrin, succinyl-β-cyclodextrin, carboxylated β-cyclodextrin, succinyl-(2-hydroxypropyl)-β-cyclodextrin, succinyl-α-cyclodextrin, heptakis(2,3,6-tri-O-benzoyl)-β-cyclodextrin, sulfated β-cyclodextrin, carboxymethyl-α-cyclodextrin, butyl-β-cyclodextrin, hexakis (2,3,6-tri-O-methyl)-α-cyclodextrin, octakis-(2,6-di-O-pentyl)-γ-cyclodextrin, octakis(2,3,6-tri-O-methyl)-γ-cyclodextrin, octakis (6-O-t-butyldimethylsilyl)-γ-cyclodextrin, butyl-γ-cyclodextrin, carboxymethyl-γ-cyclodextrin, heptakis(2,6-di-O-methyl)-β-cyclodextrin, heptakis(2,3,6-tri-O-methyl)-β-cyclodextrin, 6-monodeoxy-6-monoaminoβ-cyclodextrin, (2,6-di-O-)ethyl-β-cyclodextrin, silyl[(6-O-tert-butyldimethyl)-2,3,-di-O-acetyl]-β-cyclodextrin, heptakis(2,3,6-tri-O-ethyl)-β-cyclodextrin, hexakis(2,3,6-tri-O-octyl)-α-cyclodextrin or hexakis and (6-O-tertbutyl-dimethylsilyl)-α-cyclodextrin. More examples of CDs suitable for this invention are described in e.g., WO 2010/006392, US 2008/044364, and EP 392608, which are incorporated by reference.

In another embodiment, the nanocarriers/microcarriers used for the composition of the invention are LDEs. In particular, the LDE used for this invention comprises phosphatidylcholine, oleic acid, cholesterol, and triolein. Other liposome-like carriers known in the art can also be used.

In another embodiment, the nanocarriers used for the composition of the invention are formed of a dendrimer such as PAMAM. The table below demonstrates the size of a PAMAM dendrimer as a function of generations. More examples of dendrimers are described in, e.g., WO 2010/006392, which is incorporated by reference.

| Generation | Molecular Weight | Measured Diameter (Å) | Surface Groups |
| --- | --- | --- | --- |
| 0 | 517 | 15 | 4 |
| 1 | 1,430 | 22 | 8 |
| 2 | 3,256 | 29 | 16 |
| 3 | 6,909 | 36 | 32 |
| 4 | 14,215 | 45 | 64 |
| 5 | 28,826 | 54 | 128 |
| 6 | 58,048 | 67 | 256 |
| 7 | 116,493 | 81 | 512 |
| 8 | 233,383 | 97 | 1024 |
| 9 | 467,162 | 114 | 2048 |
| 10 | 934,720 | 135 | 4096 |

In yet another embodiment, the nanocarriers/microcarrier are liposomes (including liposomes targeted to infected cells with monoclonal antibodies to viral antigens). The liposome formulation for the compound of the present invention comprises at least one polymer, oil, at least one tensoactive and a solvent. Those skilled in the art will recognize that any suitable polymer(s), oil(s), tensoactive(s) and/or solvent(s) can be used for the liposome formulation. Determination of suitable liposome formulations for use in the present invention is within the routine skill in the art. Exemplary polymers for liposome formulation include, for example, polycaprolactone, PHB-Polyhydroxybutyrate, PMMA-Poly(methyl methacrylate), chitosane and β-Cyclodextrin. Exemplary oil used for oil phase includes, for example, isodecyl oleate, mineral oil and EMU oil. Exemplary tensoactives include, for example, sorbitan monostearate, lecithin (such as soy lecithin) and polysorbate 80. Lecithin can be any natural and/or synthetic lecithin and/or a mixture thereof. Solvents used for liposome formulation include, but are not limited to, acetone, ethanol and ultra pure water. One non-limiting example of the liposome used for the invention is liposome formed of soy or egg phosphatidylcholine (or lecithin). These can be prepared according to methods known to those skilled in the art, for example, as described in U.S. Pat. No. 4,522,811. Thus, the choices of the exact liposome formulation employed will be influenced by the cancer being treated. Certain liposome formulations will work better for some cancers than for others.

Emu oil contains several omega-6 and omega-3 fatty acids. The component present at the highest concentration is oleic acid, a monounsaturated fatty acid. Oleic acid has been known to be used as a local anti-inflammatory agent. The second most abundant fatty acid in Emu oil is linolenic acid, which has been demonstrated to alleviate muscular and joint pain. It is also rich in antioxidants, thus promoting wrinkle reduction. Compositions or pharmaceutical formulations containing Emu oil are described in e.g., CN1726926, WO991389, WO2003/018743, and WO2011/120114, which are herein incorporated by reference.

In certain embodiments, the composition of the invention includes Emu Oil or any of its components and one or more compounds selected from a cyclopentanone and/or cyclopentenone (such as a jasmonate compound or derivatives thereof), resveratrol, phosphatidylethanolamine, 10-hydroxydecenoic acid, acetogenins, plant extracts, and conjugates formed by any of the abovementioned compounds. For example, the composition contains from 0.1% to 50% by weight of Emu oil or components of Emu oil. For example, the composition includes 50% Emu oil by weight, 15% cyclopentanone or cyclopentenone by weight, 15% resveratrol by weight, 10% phosphatidylethanolamine by weight, and 10% acetogenins by weight. For example, the composition includes 50% Emu oil by weight, 30% jasmonate conjugate by weight, 10% phosphatidylethanolamine by weight, and 10% acetogenins by weight.

In certain embodiments, both the active components and the excipients are in liquid, powder and/or gel form.

In certain embodiments, the composition of the present invention contains between 5% and 90% (e.g., between 15% and 80%, between 25% and 70% or about 50%) Emu oil by weight.

In certain embodiments, the composition of the present invention contains between 1% and 30% (e.g., between 5% and 25% or between 10% and 20%, or about 15%) cyclopentanone or cyclopentenone by weight.

In certain embodiments, the composition of the present invention contains between 1% and 30% (e.g., between 5% and 25% or between 10% and 20%, or about 15%) resveratrol by weight.

In certain embodiments, the composition of the present invention contains between 1% and 20% (e.g., between 5% and 15% or about 15%) phosphatidylethanolamine by weight.

In certain embodiments, the composition of the present invention contains between 1% and 20% (e.g., between 5% and 15% or about 15%) acetogenin by weight.

In certain embodiments, the composition of the present invention contains between 5% and 60% (e.g., between 15% and 50%, or between 25% and 40%, or about 30%) conjugate by weight.

The pharmaceutical or cosmetic compositions containing Emu oil may be enriched with natural or synthetic components, such as the hybrid molecules formed by (e.g., using concepts from molecular modeling) conjugating two or more molecules, forming the so-called pro-drugs and/or the products formed by the inclusion of complexes of these pro-drugs, alone or carried or not in a variety of nano- or microcarriers or, additionally, only those molecules produced by the process described above, without Emu oil, and said molecules may or may not be carried by micro- and nanocarriers.

The pharmaceutical or cosmetic compositions containing Emu oil may also be enriched with plant extracts, including calendula oil extract, lavender essential oil, rosemary essential oil, chamomile oil, avocado oil, almond oil, wheat germ oil, passion fruit oil, grape seed oil, lavender oil, palmarosa oil, Ylang Ylang oil, chamomile oil [sic], lemon oil, carrot oil, *eucalyptus* oil, citronella essential oil, Cordia verbenacea essential oil, field mint essential oil, peppermint essential oil, *Lavandula hybrida* essential oil, lemon grass essential oil, green pepper basil essential oil, clove basil essential oil, *Cymbopogon martini* essential oil, Pogostemon cablin essential oil, Lippia Alba essential oil and *Gaultheria procumbens* essential oil.

Emu oil may be enriched with vitamins, including tocopherol, tocopheryl acetate, retinol or retinyl palmitate in their natural, mixed, synthetic or modified forms.

The pharmaceutical or cosmetic compositions obtained and described above may be enriched with natural, synthetic and/or mixed components, including hydrocarbons obtained from extracts of *Euphobia tirucalli* L. and/or *Annona muricata* L., and/or resveratrol, and/or phosphatidylethanolamine, and/or 10-hydroxydecenoic acid, and/or acetogenins, and/or albumins 1 and 2, and/or papain, in their pure or structurally modified forms, or as inclusion complexes with cyclodextrins, or carried in any other types of nano- or microcarriers.

Emu oil may be enriched or combined with other elements to strengthen its effect; for example, elements with known curative or cosmetic stabilizing effects or known to participate in the formation of products that act in a variety of ways in the process of treating or restoring diseases or aging, such as plant oils, botanic extracts, as well as active principles with proven therapeutic actions. These compounds and Emu oil may form a new hybrid molecule so that the interaction of their effects may speed up the action of Emu oil and its products on the body.

The pharmaceutical or cosmetic compositions described herein may contain liposomes prepared from the following phospholipids: dioleoylphosphatidylcholine (DOPC), dimyristoylphosphatidylcholine (DMPC), dipalmitoylphosphatidylcholine (DPPC), distearoylphosphatidylcholine (DSPC), dioleoylphosphatidylethanolamine (DOPE), distearoylphosphatidylethanolamine (DSPE), dimyristoylphosphatidylglycerol (DMPG), dipalmitoylphosphatidilglycerol (DPPG), dipalmitoylphosphatidylserine (DPPS), or distearoylphosphatidylserine (DSPS). For example, the liposomes are characterized as vesicles obtained by reverse-phase evaporation and/or with a French press and/or ether injection, with their surfaces coated or not with monosialoganglioside GM1 or phosphatidylinositol or polyethylene glycols, with their surfaces modified or not by natural and/or synthetic phosphatidylethanolamine or any kind of cholesterol and/or polyethylene glycol and/or succinimidyl-4-(N-maleimidomethyl)cyclohexane-1-carboxylate, and/or p-maleimidophenyl butyrate, as well as any dendrimer and/or polymer and/or organic elements, viruses and/or bacteria and/or fungi and/or their substrates, as well as biological elements derived from blood cells or cells from any other living animal or plant tissue, as well as diverse proteins in their natural and/or mixed and/or synthetic forms that may form nanometric and/or micrometric carrier complexes for the elements described herein.

Other examples of carriers suitable for the compositions of the invention include: simple and/or modified and/or complex and/or artificial cyclodextrins such as those called "large rings", and/or in polymers and/or dendrimers and/or liposomes that may constitute emulsions that are compatible with the active principles described herein and also with their derivatives, and/or in carbon and/or silicon nanotubes and/or carriers with crystals and/or bearers of mechanical devices to improve delivery of the carried active principle, like robotic and guided systems, and/or any nano- and/or microcarriers with such effects as to facilitate a more efficient delivery of the molecule or molecules and/or compounds to the desired target; they may also be carried by elements that themselves possess carrying potential due to synergy or modifications with other mineral and/or organic and/or mixed molecules derived from any plant and/or organic substrates of live elements such as bacteria and/or viruses and/or fungi; these may be in their simple and/or natural forms as well as modified by genetic changes and/or together with other elements and/or even added and/or subtracted, whether this process be due to changes in the basic molecular structure of the element mentioned in this patent application and/or to several other changes including: chemical and/or thermal and/or electric and/or magnetic and/or radioactive to add and/or subtract and/or increase for molecular gains as well as those of the potentials highlighted above, allowing the nano- and microcarriers to gain effects, such as magnetic and/or robotic and/or chemical and/or thermal effects that increase the efficacy of the carrying of the compounds included in this patent application to their desired targets. The main goals of the carrying processes, both micro- and nano-carrying and/or inclusion and/or complex formation, in the case of cyclodextrins, are to deliver the active principles to the cells that constitute their intended targets without them being previously degraded by the body's physiological metabolism, increasing solubility, and having low or no systemic toxicity.

In one embodiment, the size of the nanocarriers range from 1 nm to 1000 nm, e.g., 900-1000 nm, 1-900 nm, 1-800 nm, 1-700 nm, 1-600 nm, 1-500 nm, 1-400 nm, 1-300 nm, 1-200 nm, 1-150 nm, 1-100 nm, 1-90 nm, 1-80 nm, 1-70 nm, 1-60 nm, 1-50 nm, 1-40 nm, 1-30 nm, 1-20 nm, 1-10 nm, 1-5 nm, 2-300 nm, 20-200 nm, 50-150 nm, or 3.5-11 nm.

In one embodiment, the size of the microcarriers range from 2 µm to 50 µm, e.g., 2-5 µm, 2-10 µm, 2-15 µm, 2-20 µm, 2-25 µm, 2-30 µm, 2-40 µm, 2-50 µm, 5-20 µm, 5-10 µm, or 7.5-10 µm.

In one embodiment, the composition of the invention has a concentration of a jasmonate conjugate ranging from 1 nM to 100 mM, e.g., 1 nM to 99 mM, 1 nM to 90 mM, 1 nM to 80 mM, 1 nM to 70 mM, 1 nM to 60 mM, 1 nM to 50 mM, 1 nM to 40 mM, 1 nM to 30 mM, 1 nM to 20 mM, 1 nM to 10 mM, 1 nM to 5 mM, 1 nM to 1 mM, 1 nM to 900 µM, 1 nM to 800 µM, 1 nM to 700 µM, 1 nM to 600 µM, 1 nM to 500 µM, 1 nM to 400 µM, 1 nM to 300 µM, 1 nM to 200 µM, 1 nM to 100 µM, 1 nM to 90 µM, 1 nM to 80 µM, 1 nM to 70 µM, 1 nM to 60 µM, 1 nM to 50 µM, 1 nM to 40 µM, 1 nM to 30 µM, 1 nM to 20 µM, 1 nM to 10 µM, 1 nM to 5 µM, 1 nM to 1 µM, 1 nM to 900 nM, 1 nM to 800 nM, 1 nM to 700 nM, 1 nM to 600 nM, 1 nM to 500 nM, 1 nM to 400 nM, 1 nM to 300 nM, 1 nM to 200 nM, 1 nM to 100 nM, 1 nM to 90 nM, 1 nM to 80 nM, 1 nM to 70 nM, 1 nM to 60 nM, 1 nM to 50 nM, 1 nM to 40 nM, 1 nM to 30 nM, 1 nM to 20 nM, 1 nM to 10 nM, 1 nM to 5 nM, 1 nM to 1 mM, 100 nM to 1 mM, 100 nM to 100 µM, 1-100 µM, 10-50 µM, 20-30 µM, 100 µM to 10 mM, 100 µM to 100 mM, 1-100 mM, 15-70 mM, 1-100 nM, and 59-64 nM.

In one embodiment, the composition of the invention has a concentration of a jasmonate conjugate ranging from 100 mM to 1 M, e.g., from 0.2 M, 0.3 M, 0.4 M, 0.5 M, 0.6 M, 0.7 M, 0.8 M, 0.9 M to 1M, 100 mM to 1 M, 200 mM to 750 mM, or about 0.8-1 M.

In one embodiment, when the composition is used for treating leukemia, the concentration of a jasmonate conjugate included therein ranges from 100 µM to 5 mM, 100 µM to 4 mM, 100 µM to 3 mM, 100 µM to 2 mM, 100 µM to 1 mM, 100 µM to 0.5 mM, 0.01 mM to about 2 mM, or about 1 mM, 10 µM to 5 mM, 10 µM to 4 mM, 10 µM to 3 mM, or 10 µM to 2 mM. In another embodiment, when the composition is used for treating a solid tumor, the concentration of a jasmonate conjugate included therein ranges from 1 nM to 1 M (e.g., 1 nM to 0.5M, 1 nM to 0.1M, 1 nM to 50 mM, 1 nM to 10 mM, 1 nM to 5 mM, 10 nM to 1M, or 1 nM to about 1 mM, or 1 µM to 1M, or 1-1000 nM, 1-500 nM, 1-250 nM, about 1-100 nM, 1-50 nM, 1-10 nM, or 1-5 nM).

In certain embodiments, the pharmaceutically acceptable excipient or carrier is a biocompatible isotropic and anisotropic oil-in-water colloidal dispersion or a microemulsion. For example, the microemulsion comprises a surfactant, an aqueous phase, and an oil phase. For example, the surfactant is selected from soy phosphatidylcholine (e.g., Phospholipon® 90G), sodium oleate, polyoxyethylene glycerol trihydroxystearate 40 (Eumulgin® HRE40 CAS number 61788-85-0), and a mixture thereof. For example, the oil phase comprises cholesterol. For example, the microemulsion has a weight ratio of the oil phase to the surfactant ranging from 1:9 to 9:1. More examples of microemulsions are described in, e.g., Silva et al., *Int J Nanomedicine.* 2014; 9: 867-876; Oliveira et al., *Colloids Surf B Biointerfaces.* 2010; 79:372-376; and Oliveira et al., *J Pharm Sci.* 1997; 86: 616-620.

The nanocarriers or microcarriers may further contain jasmonate or non-jasmonate molecules or ions in addition to jasmonate conjugates. For example, 2-aminoethyl dihydrogen phosphate (or phosphoethanolamine), 3,7-dimethyl-2,6-octadienal (or citral), methyl salicylate, abscisic acid, natural amino acids, $Ca^{2+}$, $Zn^{2+}$, or derivatives or analogues thereof 3,7-Dimethyl-2,6-octadienal can either be a cis- or trans-isomer. These jasmonate or non-jasmonate molecules or ions can either be associated or coupled with each other, or with the jasmonate conjugates or with the nano/microcarriers. In embodiments, the active ingredients (e.g., jasmonate or non-jasmonate compounds, and conjugates) can be contained in the same or different nano/microcarriers. The association or coupling can be created via a chemical bond (e.g., a covalent bond), a hydrogen bond, a van der Waals force, a Coulomb interaction, or the like. In one embodiment, one or more active ingredients are encapsulated in the nanocarrier/microcarrier. In another embodiment, one or more active ingredients are partially encapsulated in the nanocarrier/microcarrier or at the surface of the nanocarrier/microcarrier (e.g., either as a part of the nanocarrier/microcarrier surface or outside yet attached to the surface).

As used herein, a "pharmaceutical composition" is a formulation containing a conjugate of the present invention in a form suitable for administration to a subject. In one embodiment, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the disclosed conjugate or salt, hydrate, solvate or isomer thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this invention include powders, sprays, ointments, pastes, creams, lotions, gels, solutions, patches and inhalants. In one embodiment, the nanocarried and/or microcarried active compound is mixed under sterile conditions with a pharmaceutically acceptable carrier (e.g., nanocarriers/microcarriers), and with any preservatives, buffers or propellants that are required.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, a "pharmaceutically acceptable excipient or carrier or solvent" means an excipient, carrier, or solvent that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used herein includes both one and more than one such excipient.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In a preferred aspect, the disease or condition to be treated is viral infection.

For any compound (e.g., conjugate disclosed herein), the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration in humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be expressed as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation. Dosages can range from about 0.01 mg/kg per day to about 5000 mg/kg per day. For example, dosages can range from about 0.1 mg/kg per day to about 1000 mg/kg per day. In an aspect, the dose will be in the range of about 0.1 mg/kg to about 500 mg/kg (e.g., about 1 mg/kg, 2 mg/kg, 2.5 mg/kg, 5 mg/kg, 10 mg/kg, 15 mg/kg, 20 mg/kg, 50 mg/kg, 70 mg/kg, 100 mg/kg, 140 mg/kg, 200 mg/kg, 250 mg/kg, 280 mg/kg, 300 mg/kg, 350 mg/kg, 400 mg/kg, 500 mg/kg, or 1-500 mg/kg, or 10-15 mg/kg, or 350-400 mg/kg), e.g., per day. For example, the dose will be in the range of about 0.1 mg/day to about 50 g/day; about 0.1 mg/day to about 25 g/day; about 0.1 mg/day to about 10 g/day; about 0.1 mg to about 3 g/day; or about 0.1 mg to about 1 g/day, in single, divided, or continuous doses (which dose may be adjusted for the patient's weight in kg, body surface area in $m^2$, and age in years). Determination of suitable dosages is within the routine level of skill in the art. See, e.g., Italo Mario Cesari et al., International Journal of Cell Biology Volume 2014, Article ID 572097, 25 pages, http://dx.doi.org/10.1155/2014/572097, the contents of which are hereby incorporated by reference in its entirety.

An effective amount of a pharmaceutical agent is that which provides an objectively identifiable improvement as noted by the clinician or other qualified observer. For example, regression of a tumor in a patient may be measured with reference to the diameter of a tumor. Decrease in the diameter of a tumor indicates regression. Regression is also indicated by failure of tumors to reoccur after treatment has stopped. As used herein, the term "dosage effective manner" refers to amount of an active compound to produce the desired biological effect in a subject or cell.

The pharmaceutical compositions containing nanocarried and/or microcarried active compounds of the present invention may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the nanocarried and/or microcarried active compounds into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the nanocarried and/or microcarried active compound in the required amount in an appropriate solvent with one or a combination of ingredients enumerated above, as required, followed by filtered sterilization. Generally, dispersions are prepared by incorporating the nanocarried and/or microcarried active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tablets. For the purpose of oral therapeutic administration, the nanocarried and/or microcarried active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the conjugates are delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the nanocarried and/or microcarried active compounds are formulated into ointments, salves, gels, or creams as generally known in the art.

Pharmaceutical compositions of the nanocarried and/or microcarried active compounds can be prepared with pharmaceutically acceptable carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of nanocarried and/or microcarried active compound calculated to produce the desired therapeutic effect in association with the required pharmaceutical carrier. The specification for the dosage unit forms of the invention are dictated by and directly dependent on the unique characteristics of the nanocarried and/or microcarried active compound and the particular therapeutic effect to be achieved.

The pharmaceutical compositions can be included in a container, pack, or dispenser together with instructions for administration.

The jasmonate conjugates of the present invention include their salts. All of these forms are also contemplated within the scope of the claimed invention.

As used herein, "pharmaceutically acceptable salts" refer to derivatives of the compounds of the present invention wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydroxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present invention also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, diethylamine, diethylaminoethanol, ethylenediamine, imidazole, lysine, arginine, morpholine, 2-hydroxyethylmorpholine, dibenzylethylenediamine, trimethylamine, piperidine, pyrrolidine, benzylamine, tetramethylammonium hydroxide and the like.

It should be understood that all references to pharmaceutically acceptable salts include solvent addition forms (solvates) or crystal forms (polymorphs) as defined herein, of the same salt.

The jasmonate conjugates of the present invention can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The jasmonate conjugates of the present invention can also be considered as prodrugs of jasmonate or prepared as prodrugs, for example, pharmaceutically acceptable prodrugs. The terms "pro-drug" and "prodrug" are used interchangeably herein and refer to any compound which releases an active parent drug in vivo. Since prodrugs are known to enhance numerous desirable qualities of pharmaceuticals (e.g., solubility, bioavailability, manufacturing, etc.), the conjugates of the present invention can be delivered in prodrug form. Thus, the present invention is intended to cover prodrugs of the presently claimed compounds, methods of delivering the same and compositions containing the same. "Prodrugs" are intended to include any covalently bonded carriers that release an active parent drug of the present invention in vivo when such prodrug is administered to a subject. Prodrugs in the present invention are prepared by modifying functional groups present in the compound in such a way that the modifications are cleaved, either in routine manipulation or in vivo, to the parent compound. Prodrugs include compounds of the present invention wherein a hydroxy, amino, sulfhydryl, carboxyl or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates and benzoate derivatives) and carbamates (e.g., N,N-dimethylaminocarbonyl) of hydroxy functional groups, esters (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of the invention, and the like, See Bundegaard, H., *Design of Prodrugs, p* 1-92, Elesevier, N.Y. -Oxford (1985).

The jasmonate compounds used for producing the conjugates of the present invention can also be their metabolites, such as metabolites obtained from acid and/or basic catalysis, e.g., cis-jasmonic acid, trans-jasmonic acid, hydroxymethyl cis-jasmonates, hydroxymethyl trans-jasmonates, hydroxyl cis-jasmonic acids, hydroxyl trans-jasmonic acids, lactones obtained from transesterification, and the like; metabolites obtained from oxidative reactions, e.g., ketomethyl cis-jasmonates, keto-methyltrans-jasmonates, hydroxymethyl cis-jasmonates, hydroxymethyl transjasmonates, diols obtained from oxidative reactions, stereoisomers (e.g., enantiomers or diastereoisomers) obtained from oxidative reactions, epoxides obtained from oxidative reactions, and lactones obtained from oxidative reactions; dehydration products of methyl jasmonate, jasmonic acid, and dihydromethyljasmonate; and metabolites formed through intra-cellular processes, such as phosphorylation (e.g., via kinase) or any other reaction with receptors (such as AKR2 receptor and G-protein coupled receptors), and interactions with cell organelles. Examples of MDJ metabolites include but are not limited to methyl jasmonate, methyl cucurbate, methyl 7-iso-jasmonate, 2,3-didehydro-MDJ, 3,4-didehydro-MDJ, 3,7-didehydro-MDJ, 4,5-didehydro-MDJ, 12-hydroxy-MDJ, 11-hydroxy-MDJ, 8-hydroxy-MDJ, methyl tuberonate, 12-O-glucosyl-MDJ, 11-O-glucosyl-MDJ, 12-O-glucosyl-MJ, 11-O-glucosyl-MJ, 7,8-didehydro-MDJ, cis-jasmone, dihydrojasmone, methyl salicylate, and abscisic acid.

Additionally or alternatively, other jasmonate-related compounds can be used in the formation of the conjugates of the present invention, such as those formed from linolenic acid (LA)-derived cyclopentanone- or cyclopentenone based compounds. See, e.g., *Annals of Botany* 100: 681-697, 2007; and *Annu. Rev. Plant Physiol. Plant Mol. Biol.* 1997. 48:355-81.

The pharmaceutical composition including the nanocarried and/or microcarried jasmonate conjugates, or pharmaceutically acceptable salts, esters, prodrugs or metabolites thereof, are administered orally, nasally, transdermally, pulmonary, inhalationally, buccally, sublingually, intraperitoneally, subcutaneously, intramuscularly, intravenously, rectally, intrapleurally, intrathecally and parenterally. In one embodiment, the composition is an injectable composition. One skilled in the art will recognize the advantages of certain routes of administration.

The dosage regimen is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter or arrest the progress of the condition. The dosing regimen that can be used in the methods of the invention includes, but is not limited to, daily, three times weekly (intermittent), two times weekly, weekly, or every 14 days. In certain embodiments, dosing regimen includes, but is not limited to, monthly dosing or dosing every 6-8 weeks. In certain embodiments, dosage varies during the treating period. For example, a high concentration of a jasmonate conjugate in nano/micro-carriers, ranging from 1 mM to 1 M (e.g., 1-1000 mM, 1-900 mM, 1-800 mM, 1-700 mM, 1-600 mM, 1-500 mM, 1-400 mM, 1-300 mM, 1-200 mM, 1-100 mM, 1-50 mM, 1-40 mM, 1-30 mM, 1-20 mM, 1-10 mM, 100 mM to 1 M) can be administered in the first 3 to 7 days before a lower concentration of the nano/micro-carried conjugate is administered (e.g., from 100 µM to 5 mM, 100 µM to 4 mM, 100 µM to 3 mM, 100 µM to 2 mM, 100 µM to 1 mM, 0.01 mM to about 2 mM, or about 1 mM, 10 µM to 5 mM, 10 µM to 4 mM, 10 µM to 3 mM, or 10 µM to 2 mM). In another embodiment, when the composition is used for treating a solid tumor, the concentration of a jasmonate conjugate included therein ranges from 1 nM to 1 M (e.g., 1 nM to 0.5M, 1 nM to 0.1M, 1 nM to 50 mM, 1 nM to 10 mM, 1 nM to 5 mM, 10 nM to 1M, or 1 nM to about 1 mM, or 1 µM to 1 M, or 1-1000 nM, 1-500 nM, 1-250 nM, about 1-100 nM, 1-50 nM, 1-10 nM, or 1-5 nM) for treating cancer. This dosing regimen may be more effective in treating certain type of cancer (e.g., leukemia) than the others. Alternatively, a low dose can be administered first followed by a high dose of the nano/micro-carried jasmonates.

Techniques for formulation and administration of the disclosed conjugates of the invention can be found in *Remington: the Science and Practice of Pharmacy,* 19$^{th}$ edition, Mack Publishing Co., Easton, Pa. (1995). In an embodiment, the conjugates described herein, and the pharmaceutically acceptable salts, prodrugs, metabolites, or esters thereof, are used in pharmaceutical preparations in combination with a pharmaceutically acceptable excipient, solvent or diluent. Suitable pharmaceutically acceptable excipients include inert solid fillers or diluents and sterile aqueous or organic solutions. The conjugates will be present in such pharmaceutical compositions in amounts sufficient to provide the desired dosage amount in the range described herein.

Methods of Treatment

The present invention provides methods for the treatment of a disorder the course of which is influenced by abnormal angiogenesis (or an "angiogenesis-related disorder"). The method includes administering to a subject in need of such treatment, a therapeutically effective amount of a conjugate of the present invention, or a pharmaceutically acceptable salt, prodrug, metabolite, solvate, or stereoisomeror thereof.

As used herein, a "subject in need thereof" is a subject having a disorder in which abnormal angiogenesis plays a part, or a subject having an increased risk of developing such disorder relative to the population at large. A subject in need thereof can have a precancerous condition. Preferably, a subject in need thereof has cancer. A "subject" includes a mammal. The mammal can be e.g., any mammal, e.g., a human, primate, bird, mouse, rat, fowl, dog, cat, cow, horse, goat, camel, sheep or a pig. Preferably, the mammal is a human.

One example of angiogenesis-related disorder is cancer. As used herein, the term "cancer" includes solid tumors as well as hematologic tumors and/or malignancies. Exemplary cancers include, but are not limited to, adrenocortical carcinoma, AIDS-related cancers, AIDS-related lymphoma, anal cancer, anorectal cancer, cancer of the anal canal, appendix cancer, childhood cerebellar astrocytoma, childhood cerebral astrocytoma, basal cell carcinoma, skin cancer (non-melanoma), biliary cancer, extrahepatic bile duct cancer, intrahepatic bile duct cancer, bladder cancer, uringary bladder cancer, bone and joint cancer, osteosarcoma and malignant fibrous histiocytoma, brain cancer, brain tumor, brain stem glioma, cerebellar astrocytoma, cerebral astrocytoma/malignant glioma, ependymoma, medulloblastoma, supratentorial primitive neuroectodeimal tumors, visual pathway and hypothalamic glioma, breast cancer, bronchial adenomas/carcinoids, carcinoid tumor, gastrointestinal, nervous system cancer, nervous system lymphoma, central nervous system cancer, central nervous system lymphoma, cervical cancer, childhood cancers, chronic lymphocytic leukemia, chronic myelogenous leukemia, chronic myeloproliferative disorders, colon cancer, colorectal cancer, cutaneous T-cell lymphoma, lymphoid neoplasm, mycosis fungoides, Seziary Syndrome, endometrial cancer, esophageal cancer, oesophageal cancer, extracranial germ cell tumor, extragonadal germ cell tumor, extrahepatic bile duct cancer, eye cancer, intraocular melanoma, retinoblastoma, gallbladder cancer, gastric (stomach) cancer, gastrointestinal carcinoid tumor, gastrointestinal stromal tumor (GIST), germ cell tumor, ovarian germ cell tumor, gestational trophoblastic tumor glioma, head and neck cancer, hepatocellular (liver) cancer, Hodgkin lymphoma, hypopharyngeal cancer, intraocular melanoma, ocular cancer, islet cell tumors (endocrine pancreas), Kaposi Sarcoma, kidney cancer, renal cancer, kidney cancer, laryngeal cancer, acute lymphoblastic leukemia, acute myeloid leukemia, chronic lymphocytic leukemia, chronic myelogenous leukemia, hairy cell leukemia, lip and oral cavity cancer, liver cancer, lung cancer, non-small cell lung cancer, small cell lung cancer, AIDS-related lymphoma, non-Hodgkin lymphoma, primary central nervous system lymphoma, Waldenstram macroglobulinemia, medulloblastoma, melanoma, intraocular (eye) melanoma, merkel cell carcinoma, mesothelioma malignant, mesothelioma, metastatic squamous neck cancer, mouth cancer, cancer of the tongue, multiple endocrine neoplasia syndrome, mycosis fungoides, myelodysplastic syndromes, myelodysplastic/myeloproliferative diseases, chronic myelogenous leukemia, acute myeloid leukemia, multiple myeloma, chronic myeloproliferative disorders, nasopharyngeal cancer, neuroblastoma, oral cancer, oral cavity cancer, oropharyngeal cancer, ovarian cancer, ovarian epithelial cancer, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer (prostate carcinoma or prostate adenocarcinoma, including multiple drug resistant prostate cancer), rectal cancer, renal pelvis and ureter, transitional cell cancer, retinoblastoma, rhabdomyosarcoma, salivary gland cancer, ewing family of sarcoma tumors, Kaposi Sarcoma, soft tissue sarcoma, uterine cancer, uterine sarcoma, skin cancer (non-melanoma), skin cancer (melanoma), merkel cell skin carcinoma, small intestine cancer, soft tissue sarcoma, squamous cell carcinoma, stomach (gastric) cancer, supratentorial primitive neuroectodermal tumors, testicular cancer, throat cancer, thymoma, thymoma and thymic carcinoma, thyroid cancer, transitional cell cancer of the renal pelvis and ureter and other urinary organs, gestational trophoblastic tumor, urethral cancer, endometrial uterine cancer, uterine sarcoma, uterine corpus cancer, vaginal cancer, vulvar cancer, and/or Wilm's Tumor.

Other examples of angiogenesis-related disorders include ocular diseases (e.g., age-related macular degeneration or angiogenesis-related disorders of the posterior segment of the eye), cardiovascular diseases (e.g., atherosclerosis), chronic inflammation (e.g., rheutatoid arthritis or Crohn's disease), diabetes (e.g., diabetic retinopathy), psoriasis, endometriosis, and adiposity. See, e.g., *Pharmacological Reviews* 52: 237 268, 2001.

The present invention provides methods for the treatment of an NF-κB-related disorder, such as a viral, bacterial, or fungal infection. The method includes administering to a subject in need of such treatment, a therapeutically effective amount of a conjugate of the present invention, or a pharmaceutically acceptable salt, prodrug, metabolite, solvate, or stereoisomeror thereof.

The present invention provides methods for the treatment of wounds, burns and skin or aesthetic treatments. The method includes administering to a subject in need of such treatment, a therapeutically effective amount of a conjugate of the present invention, or a pharmaceutically acceptable salt, prodrug, metabolite, solvate, or stereoisomeror thereof.

As used herein, "treating" or "treat" describes the management and care of a patient for the purpose of combating a disease, condition, or disorder and includes the administration of a conjugate of the present invention, or a pharmaceutically acceptable salt, prodrug, metabolite, or solvate thereof, to alleviate the symptoms or complications of a disease, condition or disorder, or to eliminate the disease, condition or disorder.

A conjugate of the present invention, or a pharmaceutically acceptable salt, prodrug, metabolite, or solvate thereof, can also be used to prevent a disease, condition or disorder. As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of pharmaceutical compositions of the invention leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

The conjugates of the present invention and the compounds or derivatives thereof that are used for making the conjugates of the present invention can be prepared in a variety of ways using commercially available starting materials, compounds known in the literature, or from readily prepared intermediates, by employing standard synthetic methods and procedures either known to those skilled in the art, or which will be apparent to the skilled artisan in light of the teachings herein. Standard synthetic methods and procedures for the preparation of organic molecules and functional group transformations and manipulations may be obtained from the relevant scientific literature or from standard textbooks in the field. Although not limited to any one or several sources, classic texts such as Smith, M. B., March, J., *March's Advanced Organic Chemistry: Reactions, Mechanisms, and Structure*, $5^{th}$ edition, John Wiley & Sons: New York, 2001; and Greene, T. W., Wuts, P. G. M., *Protective Groups in Organic Synthesis*, $3^{rd}$ edition, John Wiley & Sons: New York, 1999, incorporated by reference herein, are useful and recognized reference textbooks of organic synthesis known to those in the art.

Conjugates of the present invention and the starting compounds for producing the conjugates can be conveniently prepared by a variety of methods familiar to those skilled in the art. The conjugates or hybrid compounds of this invention with each of the formulae described herein may be prepared from commercially available starting materials or starting materials which can be prepared using literature procedures.

Conjugates or hybrid compounds designed, selected and/or optimized by methods described herein, once produced, can be characterized using a variety of assays known to those skilled in the art to determine whether the conjugates have biological activity. For example, the conjugates can be characterized by conventional assays, including but not limited to the assays described in U.S. Pat. No. 8,883,220, to determine whether they have a predicted activity, binding activity and/or binding specificity.

One skilled in the art may refer to general reference texts for detailed descriptions of known techniques discussed herein or equivalent techniques. These texts include Ausubel et al., *Current Protocols in Molecular Biology*, John Wiley and Sons, Inc. (2005); Sambrook et al., *Molecular Cloning, A Laboratory Manual* ($3^{rd}$ edition), Cold Spring Harbor Press, Cold Spring Harbor, N.Y. (2000); Coligan et al., *Current Protocols in Immunology*, John Wiley & Sons, N.Y.; Enna et al., *Current Protocols in Pharmacology*, John Wiley & Sons, N.Y.; Fingl et al., *The Pharmacological Basis of Therapeutics* (1975), Remington's Pharmaceutical Sciences, Mack Publishing Co., Easton, Pa., $18^{th}$ edition (1990). These texts can, of course, also be referred to in making or using an aspect of the invention.

Furthermore, high-throughput screening can be used to speed up analysis using such assays. As a result, it can be possible to rapidly screen the conjugate molecules described herein for activity, using techniques known in the art. General methodologies for performing high-throughput screening are described, for example, in Devlin (1998) *High Throughput Screening*, Marcel Dekker; and U.S. Pat. No. 5,763,263. High-throughput assays can use one or more different assay techniques including, but not limited to, those described below.

All patents, patent applications, and publications mentioned herein are hereby incorporated by reference in their entireties. However, where a patent, patent application, or publication containing express definitions is incorporated by reference, those express definitions should be understood to apply to the incorporated patent, patent application, or publication in which they are found, and not to the remainder of the text of this application, in particular the claims of this application.

It is to be understood that while the invention has been described in conjunction with the preferred specific embodiments thereof, that the foregoing description as well as the examples that follow, are intended to illustrate and not limit the scope of the invention. It will be understood by those skilled in the art that various changes may be made and equivalents may be substituted without departing from the scope of the invention, and further that other aspects, advantages and modifications will be apparent to those skilled in the art to which the invention pertains.

All percentages and ratios used herein, unless otherwise indicated, are by weight. Other features and advantages of the present invention are apparent from the different examples. The provided examples illustrate different components and methodology useful in practicing the present invention. The examples do not limit the claimed invention. Based on the present disclosure the skilled artisan can identify and employ other components and methodology useful for practicing the present invention.

EXAMPLES

Several jasmonate conjugates were produced using the methods described herein. The molar ratio of the starting materials for the target conjugate was about 1. For example, when making a jasmonate-resveratrol conjugate, the molar ratio between a jasmonate (e.g., MJ or MDJ) and resveratrol was 1:1; when making a jasmonate-Coenzyme Q10 conjugate, the molar ratio between a jasmonate (e.g., MJ or MDJ) and Coenzyme Q10 was 1:1; and when making a jasmonate-bitter gourd component conjugate, the molar ratio between a jasmonate (e.g., MJ or MDJ) and a bitter gourd component was 1:1.

The concentration range of the jasmonate conjugate is controlled at between $10^{-9}$ M and 0.005 M (e.g., about 0.00468 mol in vivo, or 17.63 mM-66.8 mM). All formulations prepared included B-cyclodextrin. For example, in a mouse model study, a formulation containing MDJ or conjugate thereof, in various amounts equivalent to from about 1-500 mg (e.g., 10-15 mg to about 350-400 mg) of MDJ per kilogram of the body weight is administered to mice. More specifically, male Swiss mice, weighing about 30 g, are divided into several groups of five animals: a few experimental groups for MJ or MDJ-conjugates; a few experimental groups for a mixture of MJ or MDJ with another compound such as resveratrol, Coenzyme Q10, and a bitter gourd component (i.e., an unconjugated mixture); a few control groups (e.g., one for vehicle (e.g., solvent used for making the formulations such as a saline solution), one for a mixture of vehicle and MJ or MDJ, and another for a mixture of vehicle and the nanocarriers and/or microcarriers used, e.g., cyclodextrin). The experimental groups receive, by single intraperitoneal injection, doses between 1 mg/kg and 500 mg/kg equivalent of MJ or MDJ (e.g., 70 mg/kg, 140 mg/kg, 280 mg/kg, and 350 mg/kg). The control groups receive the vehicle or the mixtures noted above. The animals are observed for a few days after administrations for any obvious symptoms and mortality. The results are considered positive if death occurred in 50% of test animals with one of the administered doses. More detail of the in vivo study is described in Gisela Bevilacqua Rolfsen Ferreira da Silva et al., International Journal of Nanomedicine 2015:10 585-594, the contents of which are incorporated herein by reference in its entirety.

The invention can be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

I claim:
1. A conjugate

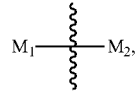

in which $M_1$ is a jasmonate compound, wherein the jasmonate compound is selected from the group consisting of jasmonic acid, 7-iso-jasmonic acid, 9,10-dihydrojasmonic acid, 9,10-dihydro-isojasmonic acid, 2,3-didehydrojasmonic acid, 3,4-didehydrojasmonic acid, 3,7-didehydrojasmonic acid, 4,5-didehydrojasmonic acid, 4,5-didehydro-7-isojasmonic acid, cucurbic acid, 6-epi-cucurbic acid, 6-epi-cucurbic acid-lactone, 12-hydroxy-jasmonic acid, 12-hydroxy-jasmonic acid-lactone, 11-hydroxy-jasmonic acid, 8-hydroxyjasmonic acid, homo-jasmonic acid, dihomo-jasmonic acid, 11-hydroxy-dihomo-jasmonic acid, 8-hydroxy-dihomo-jasmonic acid, tuberonic acid, tuberonic acid-O-β-glucopyranoside, cucurbic acid-O-β-glucopyranoside, 5,6-didehydro-jasmonic acid, 6,7-didehydro-jasmonic acid, 7,8-didehydro-jasmonic acid, cis-jasmone, dihydrojasmone, and a lower alkyl ester thereof, $M_2$ is a compound different from $M_1$ and is covalently attached to $M_1$ and

between $M_1$ and $M_2$ denotes direct attachment of $M_2$ to $M_1$, wherein the conjugate is contained within a nanocarrier, wherein $M_2$ is selected from resveratrol, a gambogic acid, perillyl alcohol, curcumin, a flavonoid, 10-hydroxydecenoic acid, acetogenin, phosphatidylethanolamine, a chemical component of propolis selected from caffeic acid, cinnamic acid, 3,5-diprenyl-4-hydroxycinnamic acid (artepillin C), and esters thereof, and caffeic acid, phenethyl ester (CAPE), a chemical component of Emu oil selected from stearic acid, oleic acid and linolenic acid, and esters thereof, a chemical component or an extract of bitter gourd (Momordica charantia) selected from momordin, saponin, charantin, momordicosides A, B, F1, F2, K, L, M, N, and S, charantosides I through VIII, karavilosides I, II, III, V, and XI, MAP30 and MCP30 proteins, kuguaglycoside A through H, goyaglycosides c and d, beta carotene, ascorbic acid, niacin, thiamin, and Coenzyme Q 10.

2. The conjugate of claim 1, wherein the conjugate is of Formula (I):

(I)

wherein
n is 1, 2, 3, or 4;
X is O or S;
Y is O, or NH;
each occurrence of Z independently is CH or N;
$R_1$ is H, alkyl, alkenyl, or alkynyl;
each occurrence of $R_2$, $R_3$, $R_4$, $R_5$, $R_6$, $R_7$, $R_8$, $R_9$, $R_{10}$, $R_{11}$, and $R_{12}$ independently is H, $NH_2$, $NHCOR_{13}$, $-N=CHR_{14}$, $-N=CH-R_{13}$, $-NHCH_2R_{15}$, $-NHCH_2R_{13}$, $-NHSO_2R_{15}$, $-NHCONHR_{15}$, $-N=CHR_{16}$, $-COOR_{16}$, $-CONR_{16}R_{16}$, $-CONR_{16}R_{15}$, $-CN$, $-COCH_2Cl$, $-CONHNH_2$, $R_{17}$, $R_{16}$, $-OR_{16}$, $-SR_{16}$, $-NO_2$, $-COR_{16}$, $-NO$, $-N_3$, $-OCN$, $-NCS$, $-COOR_{16}$, $-COCN$, $-NR_{16}R_{16}$, $-SOR_{16}$, $-SO_2R_{16}$, $-SO_3R_{16}$, $-CH_2OR_{16}$,

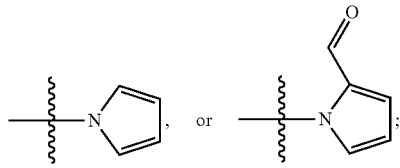 [SMILES: *n1cccc1 ; *n1cccc1C=O]

alternatively, when valence permits, any two neighboring $R_{11}$ or neighboring $R_{11}$ and $R_{12}$, together with the two carbon atoms to which they attach, form a carbon-carbon double bond or a cycloalkyl, cycloalkenyl, aryl, heterocycloalkyl, or heteroaryl group;
$R_{13}$ is $R_{14}$, $R_{16}$, $-CH_2OR_{15}$, $-CH=CHR_{15}$, $-CH_2CHR_{15}COR_{16}$, $-C_2H_4OR_{15}$, $-C_3H_6OR_{15}$, $-C_2H_4SCOR_{16}$, $-CH_2SCOR_{16}$, $-COOR_{16}$, $-CH_2S-R_{18}$, $-CH_2-R_{18}$, $-CH=CH-R_{18}$, in which $R_{18}$ is cycloalkyl, 5- or 6-membered heteroaryl, or 5- to 12-memebered heterocycloalkyl and $R_{18}$ is optionally substituted with one or more of $-COOR_{16}$, $R_{16}$ and $R_{17}$;
$R_{14}$ is phenyl optionally substituted with one or more $R_{16}$;
$R_{15}$ is phenyl optionally substituted with one or more substituents selected from $R_{13}$ and $R_{16}$;
$R_{16}$ is H, alkyl optionally substituted with halo or hydroxyl, alkenyl, phenyl, or $-CH_2R_{14}$; and
$R_{17}$ is halo.

3. The conjugate of claim 2, wherein the conjugate is of Formula (Ia) or (Ib):

(Ia)

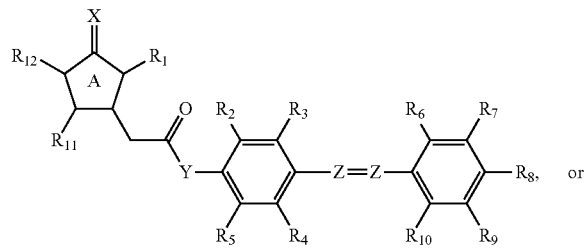

or (Ib)

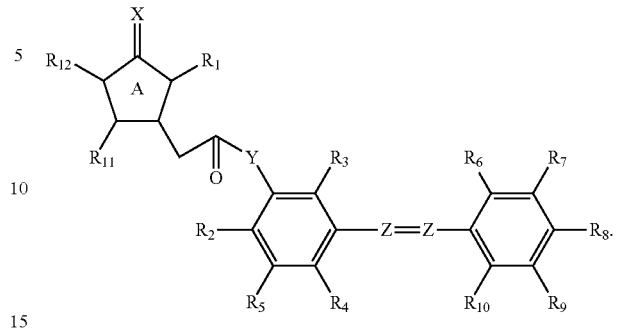

4. A composition comprising a carrier and a conjugate of claim 1.

5. The composition of claim 4, being a pharmaceutical composition and the carrier is a pharmaceutically acceptable carrier.

6. The composition of claim 4, being a cosmetic composition and the carrier is a cosmetically acceptable carrier.

7. A method of treating disorder, comprising administering an effective amount of a conjugate of claim 1 in a subject in need thereof.

8. The method of claim 7, wherein the disorder is cancer.

9. The method of claim 8, wherein the cancer is leukemia, colon cancer, breast cancer, prostate cancer, pancreas cancer, liver cancer, skin cancer, ovary cancer, melanoma, or a sarcoma.

10. The method of claim 7, wherein the disorder is an inflammatory disease.

11. The method of claim 10, wherein the inflammatory disease is inflammatory bowel disease.

12. The method of claim 7, wherein the disorder is caused by NF-κB-activation.

13. The method of claim 12, wherein the disorder is a viral, bacterial, or fungal infection.

14. The conjugate of claim 1, wherein the nanocarrier is comprised of cyclodextrin, a liposome, or synthetic nanoemulsion particles (LDEs) comprising a cholesteryl ester core surrounded by a phospholipid outer layer.

15. The conjugate of claim 14, wherein the nanocarrier further comprises one or more of phosphoethanolamine, 3,7-dimethyl-2,6-octadienal, methyl salicylate, abscisic acid, natural amino acids, $Ca^{2+}$, $Zn^{2+}$.

* * * * *